US007989498B2

(12) United States Patent
Saunders et al.

(10) Patent No.: US 7,989,498 B2
(45) Date of Patent: *Aug. 2, 2011

(54) INHIBITORS OF IMPDH ENZYME

(75) Inventors: Jeffrey O Saunders, Acton, MA (US); Daniel Elbaum, Newton, MA (US); Perry M Novak, Milford, MA (US); Douglas Naegele, Washington, DC (US); Randy S Bethiel, Bedford, MA (US); Steven M Ronkin, Watertown, MA (US); Michael C Badia, Bedford, MA (US); Catharine Frank, Langhorne, PA (US); Dean P Stamos, Framingham, MA (US); William Walters, Waltham, MA (US); David Pearlman, Arlington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/671,967

(22) Filed: Sep. 25, 2003

(65) Prior Publication Data

US 2004/0087650 A1    May 6, 2004

Related U.S. Application Data

(60) Division of application No. 09/702,991, filed on Oct. 30, 2000, now Pat. No. 6,653,309, which is a continuation of application No. PCT/US99/09005, filed on Apr. 26, 1999.

(51) Int. Cl.
*A61K 31/165* (2006.01)
*A61K 31/16* (2006.01)

(52) U.S. Cl. ........ 514/616; 514/374; 514/468; 514/522; 514/535; 514/580; 514/617

(58) Field of Classification Search .................. 564/173, 564/184; 514/173, 374, 468, 522, 535, 580, 514/604, 616, 617
See application file for complete search history.

(56) References Cited

U.S. PATENT DOCUMENTS

| | | | | |
|---|---|---|---|---|
| 1,935,554 | A | 11/1933 | Grether et al. | 564/140 |
| 2,025,116 | A | 12/1935 | Lubs et al. | 564/140 |
| 2,965,575 | A * | 12/1960 | Beaver et al. | 510/387 |
| 3,064,049 | A | 11/1962 | Cox et al. | 564/173 |
| 3,573,051 | A * | 3/1971 | Gray | 430/172 |
| 3,973,038 | A | 8/1976 | Umezawa et al. | |
| 4,028,394 | A | 6/1977 | Karsten et al. | |
| 4,242,260 | A | 12/1980 | Sasaki et al. | 260/160 |
| 5,070,096 | A | 12/1991 | Mohrs et al. | |
| 5,093,340 | A | 3/1992 | Mohrs et al. | |
| 5,380,879 | A | 1/1995 | Sjogren | 549/310 |
| 5,446,010 | A | 8/1995 | Toyofuku et al. | |
| 5,712,298 | A * | 1/1998 | Amschler | 514/352 |
| 5,721,246 | A | 2/1998 | Yoshino et al. | |
| 6,071,968 | A * | 6/2000 | Nishino et al. | 514/617 |
| 6,653,309 | B1 * | 11/2003 | Saunders et al. | 514/242 |

FOREIGN PATENT DOCUMENTS

| | | |
|---|---|---|
| CA | 1041502 | 10/1978 |
| CA | 1206964 | 7/1986 |
| CH | 332480 | 9/1958 |
| DE | 838 290 | 5/1950 |
| EP | 0051819 | 2/1985 |
| EP | 0211568 B1 | 10/1989 |
| EP | 0221346 B1 | 1/1991 |
| EP | 0279633 B1 | 4/1993 |
| EP | 0610653 B1 | 4/1997 |
| EP | 0673937 B1 | 11/2003 |
| FR | 1584606 | 7/1968 |
| GB | 1459142 | 12/1976 |
| JP | 49-102693 | 9/1974 |
| JP | 49-127939 | 12/1974 |
| JP | 57-122039 | 7/1982 |
| JP | 62-029562 | 2/1987 |
| JP | 62-081359 | 4/1987 |
| JP | 63-093765 | 4/1988 |
| JP | 63-222152 | 9/1988 |
| JP | 06-199047 | 7/1994 |
| JP | 06-297860 | 10/1994 |
| JP | 07-165708 | 6/1995 |
| JP | 08-143525 | 6/1996 |
| JP | 08-512041 | 12/1996 |
| JP | 09-157236 | 6/1997 |
| WO | WO 97/40028 | 10/1997 |
| WO | WO 99/55663 | 11/1999 |

OTHER PUBLICATIONS

Buu-Hoi et al, Bull. de la Soc. Chim. de France(1947), 128-36.*
Carter et al., Chemotherapy of Cancer, second edition, John Wiley & Sons, N.Y., N.Y., 1981, pp. 362-365.*
Barr et al., "Indoaniline dyes", *Chemical Abstracts*, (1961) 55:24.
Boit, Hans-G.: "Beilsteins Handbuch der Organischen Chemie, 4th Ed. Suppl. III vol. 13" 1973, Springer Verlag, Berlin, Heidelberg, New York XP002111106 p. 837, para. 4; p. 838, para. 2; p. 2155, para. 3.
Hochuli et al., "Printing of nontextile sheets", *Chemical Abstracts*, (1959) 53:15.
Kekre et al., "Syntheses and biological activity of 1,3-naphthoxazine-2,4-diones", 123834n *Chemical Abstracts*, (1976) 85:17.

(Continued)

*Primary Examiner* — Shailendra Kumar
(74) *Attorney, Agent, or Firm* — Ropes & Gray LLP; James F. Haley, Jr.

(57) ABSTRACT

The present invention relates to compounds which inhibit IMPDH. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH mediated processes. This invention also relates to methods for inhibiting the activity of IMPDH using the compounds of this invention and related compounds.

1 Claim, No Drawings

OTHER PUBLICATIONS

Kishimoto et al., "Synthesis of anilide derivatives of 1-hydroxy-2=naphthoic acid", *Chemical Abstracts*, (1988) 108:5.

Luckenbach, Reiner: "Beilsteins Handbuch der Organischen Chemie, 4$^{th}$ Ed. Suppl. II vol. 13" 1985, Springer Verlag, Berlin, Heidelberg, New York XP002111107 p. 1717, para. 1,2.

Mullink et al., "Combined immuno- and non-radioactive hybridocytochemistry on cells and tissue sections: influence of fixation, enzyme pretreatment, and choice of chromogen on detection of antigen and DNA sequences" 228120q *Chemical Abstracts*, (1989) 110:25, p. 317.

Nishino et al., "Azo dyes derived from catechol", *Chemical Abstracts*, (1959) 53:12.

Patani et al., "Bioisosterism: A Rational Approach in Drug Design", *Chem. Rev.*, 1996 96:3147-76.

Richter, Friedrich: "Beilsteins Handbuch der Organischen Chemie, 4$^{th}$ Ed. Suppl. II vol. 13" 1950, Springer Verlag, Berlin, Göttingen, Heidelberg (DE) XP002111105 pg. 181, para. 6.

Sebe et al., "Organic pigments—AS-RS napthol derivatives", *Chemical Abstracts*, (1989) 110:24, p. 103.

Solomons et al., *Anti-Cancer Drugs Des.* (1997) 12 (98):635-647.

Webber et al., "A quantitative cytochemical assay for osteoclast acid phosphatase activity in fetal rat calvaria", 110:3327n *Chemical Abstracts*, (1989) 110:1, p. 309.

Allay et al., "Sensitization of hematopoietic stem and progenitor cells to trimetrexate using nucleoside transport inhibitors," *Blood*, 90(9):3546-3554 (1997).

Cechinel-Filho et al., "Synthesis of xanthoxyline derivatives with antinociceptive and antioedematogenic activities," *European Journal of Medicinal Chemistry*, 31(10):833-839 (1996).

Chen et al., "Structure-activity relationships in a series of 5-[(2,5-dihydroxybenzyl)amino]salicylate inhibitors of EGF-receptor-associated tyrosine kinase: importance of additional hydrophobic aromatic interactions," *Journal of Medicinal Chemistry*, 37(6):845-859 (1994).

Chio et al., "Identification of a class of sulfonamides highly active against dihydropteroate synthase form *Toxoplasma gondii*, *Pneumocystis carinii*, and *Mycobacterium avium*," *Antimicrobial Agents and Chemotherapy*, 40(3):727-733 (1996).

Cushman et al., "Synthesis and evaluation of stilbene and dihydrostilbene derivatives as potential anticancer agents that inhibit tubulin polymerization," *Journal of Medicinal Chemistry*, 34(8):2579-2588 (1991).

Hong et al., "Inhibition of recombinant Pneumocystis carinii dihydropteroate synthetase by sulfa drugs," *Antimicrobial Agents and Chemotherapy*, 39(8):1756-1763 (1995).

Linfield et al., "Antibacterially active substituted anilides of carboxylic and sulfonic acids," *Journal of Medicinal Chemistry*, 26(12):1741-1746 (1983).

Patakoot et al., "Preparation of some aryla of o, m and p—cresotic acids," *Journal of the University of Bombay, Science: Physical Sciences, Mathematics, Biological Sciences and Medicine Section A*, 25(40):13-14 (1957).

Ramana et al., "Synthesis of 2-substituted benzoxazoles and benzimidazoles based on mass spectral *ortho* interactions" *Journal of the Chemical Society, Perkin Transactions 2*: (7):1497-501 (1995).

Grammaticakis, "No. 165.—Contribution to the study of the absorption in the middle ultraviolet range and the visible range of N-aroyl-arylamines. III.—o-, m-, p- methoxybenzoylalkoylamines and o-, m-, p- methoxybenzoylarylamines," *Bulletin de la Societe Chimique de France*, 5:924-935 (1964) (English Language Abstract Attached).

Weuffen et al., "Investigation of 2-Hydroxythiobenzamides and 2-Hydroxythiobenzanilides. 4th Communication: Preliminary Investigations to Determine the Anthelminthic Efficacy of the Substances," *Pharmazie*, 23(6):308-310 (1968) (English Language Summary Attached).

* cited by examiner

INHIBITORS OF IMPDH ENZYME

TECHNICAL FIELD OF THE INVENTION

The present invention relates to compounds which inhibit IMPDH. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH mediated processes. This invention also relates to methods for inhibiting the activity of IMPDH using the compounds of this invention and related compounds.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanosine nucleotides. IMPDH catalyzes the NAD-dependent oxidation of inosine-5'-monophosphate (IMP) to xanthosine-5'-monophosphate (XMP) [Jackson R. C. et. al., *Nature*, 256, pp. 331-333, (1975)].

IMPDH is ubiquitous in eukaryotes, bacteria and protozoa [Y. Natsumeda & S. F. Carr, *Ann. N.Y. Acad.*, 696, pp. 88-93 (1993)]. The prokaryotic forms share 30-40% sequence identity with the human enzyme. Regardless of species, the enzyme follows an ordered Bi—Bi reaction sequence of substrate and cofactor binding and product release. First, IMP binds to IMPDH. This is followed by the binding of the cofactor NAD. The reduced cofactor, NADH, is then released from the product, followed by the product, XMP [S. F. Carr et al., *J. Biol. Chem.*, 268, pp. 27286-90 (1993); E. W. Holmes et al., *Biochim. Biophys. Acta*, 364, pp. 209-217 (1974)]. This mechanism differs from that of most other known NAD-dependent dehydrogenases, which have either a random order of substrate addition or require NAD to bind before the substrate.

Two isoforms of human IMPDH, designated type I and type II, have been identified and sequenced [F. R. Collart and E. Huberman, *J. Biol. Chem.*, 263, pp. 15769-15772, (1988); Y. Natsumeda et. al., *J. Biol. Chem.*, 265, pp. 5292-5295, (1990)]. Each is 514 amino acids, and they share 84% sequence identity. Both IMPDH type I and type II form active tetramers in solution, with subunit molecular weights of 56 kDa [Y. Yamada et. al., *Biochemistry*, 27, pp. 2737-2745 (1988)].

The de novo synthesis of guanosine nucleotides, and thus the activity of IMPDH, is particularly important in B and T-lymphocytes. These cells depend on the de novo, rather than salvage pathway to generate sufficient levels of nucleotides necessary to initiate a proliferative response to mitogen or antigen [A. C. Allison et. al., *Lancet II*, 1179, (1975) and A. C. Allison et. al., *Ciba Found. Symp.*, 48, 207, (1977)]. Thus, IMPDH is an attractive target for selectively inhibiting the immune system without also inhibiting the proliferation of other cells.

Immunosuppression has been achieved by inhibiting a variety of enzymes including for example, the phosphatase calcineurin (inhibited by cyclosporin and FK-506); dihydroorotate dehydrogenase, an enzyme involved in the biosynthesis of pyrimidines (inhibited by leflunomide and brequinar); the kinase FRAP (inhibited by rapamycin); and the heat shock protein hsp70 (inhibited by deoxyspergualin). [See B. D. Kahan, *Immunological Reviews*, 136, pp. 29-49 (1993); R. E. Morris, *The Journal of Heart and Lung Transplantation*, 12(6), pp. S275-S286 (1993)].

Inhibitors of IMPDH are also known. U.S Pat. Nos. 5,380,879 and 5,444,072 and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B and T-cells to mitogen or antigen [A. C. Allison et. al., *Ann. N. Y. Acad. Sci.*, 696, 63, (1993).

Immunosuppressants, such as MPA, are useful drugs in the treatment of transplant rejection and autoimmune diseases. [R. E. Morris, *Kidney Intl.*, 49, Suppl. 53, S-26, (1996)]. However, MPA is characterized by undesirable pharmacological properties, such as gastrointestinal toxicity and poor bioavailability. [L. M. Shaw, et. al., *Therapeutic Drug Monitoring*, 17, pp. 690-699, (1995)].

In addition, U.S. Pat. No. 6,054,472 (which corresponds to PCT publication WO 97/40028) describes a novel class of compounds and pharmaceutical compositions which inhibit IMPDH. The described invention also relates to methods for inhibiting the activity of IMPDH using the compounds and pharmaceutical compositions and related compounds contained therein. Because the compounds described in this patent demonstrate a different metabolic profile than MPA and its derivatives, methods of this invention and the compounds used therein may offer advantages as therapeutics for IMPDH mediated disease. These advantages include increased overall therapeutic benefit and reduction in deleterious side effects.

Nucleoside analogs such as tiazofurin, ribavirin and mizoribine also inhibit IMPDH [L. Hedstrom, et. al. *Biochemistry*, 29, pp. 849-854 (1990)]. These, compounds, which are competitive inhibitors of IMPDH, suffer from lack of specificity to this enzyme.

Mycophenolate mofetil, a prodrug which quickly liberates free MPA in vivo, was recently approved to prevent acute renal allograft rejection following kidney transplantation. [L. M. Shaw, et. al., *Therapeutic Drug Monitoring*, 17, pp. 690-699, (1995); H. W. Sollinger, *Transplantation*, 60, pp. 225-232 (1995)]. Several clinical observations, however, limit the therapeutic potential of this drug. [L. M. Shaw, et. al., *Therapeutic Drug Monitoring*, 17, pp. 690-699, (1995)]. MPA is rapidly metabolized to the inactive glucuronide in vivo. [A. C. Allison and E. M. Eugui, *Immunological Reviews*, 136, pp. 5-28 (1993)]. The glucuronide then undergoes enterohepatic recycling causing accumulation of MPA in the gastrointestinal tract where it cannot exert its IMPDH inhibitory activity on the immune system. This effectively lowers the drug's in vivo potency, while increasing its undesirable gastrointestinal side effects.

More recently, IMPDH inhibitors of a different class have been described in PCT publication WO 97/40028.

It is also known that IMPDH plays a role in other metabolic events. Increased IMPDH activity has been observed in rapidly proliferating human leukemic cell lines and other tumor cell lines, indicating IMPDH as a target for anti-cancer as well as immunosuppressive chemotherapy [M. Nagai et. al., *Cancer Res.*, 51, pp. 3886-3890, (1991)]. IMPDH has also been shown to play a role in the proliferation of smooth muscle cells, indicating that inhibitors of IMPDH, such as MPA or rapamycin, may be useful in-preventing restenosis or other hyperproliferative vascular diseases [C. R. Gregory et al.,

*Transplantation*, 59, pp. 655-61 (1995); PCT publication WO 94/12184; and PCT publication WO 94/01105].

Additionally, IMPDH has been shown to plays a role in viral replication in some viral cell lines. [S. F. Carr, *J. Biol. Chem.*, 268, pp. 27286-27290 (1993)]. Analogous to lymphocyte and tumor cell lines, the implication is that the de novo, rather than the salvage, pathway is critical in the process of viral replication.

Thus, there remains a need for potent IMPDH inhibitors with improved pharmacological properties. Such inhibitors would have therapeutic potential as immunosuppressants, anti-cancer agents, anti-vascular hyperproliferative agents, anti-inflammatory agents, antifungal agents, antipsoriatic and anti-viral agents.

SUMMARY OF THE INVENTION

The present invention provides compounds, and pharmaceutically acceptable derivatives thereof, that are useful as inhibitors of IMPDH. These compounds can be used alone or in combination with other therapeutic or prophylactic agents, such as anti-virals, anti-inflammatory agents, antibiotics, and immunosuppressants for the treatment or prophylaxis of transplant rejection and autoimmune disease.

Additionally, these compounds are useful, alone in combination with other agents, as therapeutic and prophylactic agents for antiviral, anti-tumor, anti-cancer, anti-inflammatory agents, antifungal agents, antipsoriatic immunosuppressive chemotherapy and restenosis therapy regimens.

The invention also provides pharmaceutical compositions comprising the compounds of this invention, as well as multi-component compositions comprising additional IMPDH compounds together with an immunosuppressant. The invention also provides methods of using the compounds of this invention, as well as other related compounds, for the inhibition of IMPDH.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bn | benzyl |
| CDI | carbonyldiimidazole |
| DIEA | diisopropylethylamine |
| DMAP | dimethylaminopyridine |
| DMF | dimethylformamide |
| DMSO | dimethylsulfoxide |
| EDC | 1-(3-dimethylaminopropyl)-3-ethylcarbodiimide hydrochloride |
| EtoAc | ethyl acetate |
| THF | tetrahydrofuran |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The terms "halo" or "halogen" refer to a radical of fluorine, chlorine, bromine or iodine.

The term "immunosuppressant" refers to a compound or drug which possesses immune response inhibitory activity.

Examples of such agents include cyclosporin A, FK506, rapamycin, leflunomide, deoxyspergualin, prednisone, azathioprine, mycophenolate mofetil, OKT3, ATAG, interferon and mizoribine.

The term "interferon" refers to all forms of interferons, including but not limited to alpha, beta and gamma forms.

IMPDH-mediated disease refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as inflammatory diseases, cancer, viral replication diseases and vascular diseases.

For example, the compounds, compositions and methods of using them of this invention may be used in the treatment of transplant rejection (e.g., kidney, liver, heart, lung, pancreas (islet cells), bone marrow, cornea, small bowel and skin allografts and heart valve xenografts), rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, hepatitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, and glomerulonephritis, scleroderma, lichen planus, viteligo (depigmentation of the skin), autoimmune thyroiditis, and alveolitis, inflammatory diseases such as osteoarthritis, acute pancreatitis, chronic pancreatitis, asthma and adult respiratory distress syndrome, as well as in the treatment of cancer and tumors, such as solid tumors, lymphomas and leukemia, vascular diseases, such as restenosis, stenosis and atherosclerosis, and DNA and RNA viral replication diseases, such as retroviral diseases, and herpes.

Additionally, IMPDH enzymes are also known to be present in bacteria and thus may regulate bacterial growth. As such, the IMPDH-inhibitor compounds, compositions and methods described herein may be useful in treatment or prevention of bacterial infection, alone or in combination with other antibiotic agents.

The term "treating" as used herein refers to the alleviation of symptoms of a particular disorder in a patient or the improvement of an ascertainable measurement associated with a particular disorder. As used herein, the term "patient" refers to a mammal, including a human.

The terms "HBV", "HCV" and "HGV" refer to hepatitis-B virus, hepatitis-C virus and hepatitis-G virus, respectively.

According to one embodiment, the invention provides compounds of formula I:

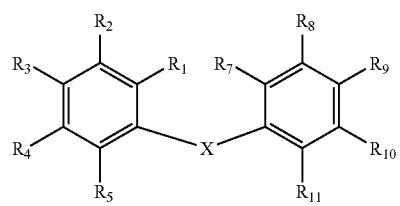

wherein:

X is selected from —C(O)—N($R_6$)—, —N($R_6$)—C(O)—, —$C_2$—N($R_6$)—, —N($R_6$)—$CH_2$—, —N($R_6$) —$S(O)_2$—, —$S(O)_2$—N($R_6$)—, —C($R_{12}$)($R_{12}$)—C (O)—, —C(O)—C($R_{12}$)($R_{12}$)—, —C($R_2$)($R_{12}$)—S(O)$_2$—, —S(O)$_2$—C($R_{12}$)($R_{12}$)—, —S(O)$_2$—O—, —O—S(O)$_2$—, —N($R_6$)—C(O)—Y— or —Y—C(O)—N($R_6$)—; wherein each $R_6$ is independently selected from hydrogen, $C_1$-$C_4$ straight or branched alkyl, $C_2$-$C_4$ straight or branched alkenyl or alkynyl, Ar-substituted-$C_1$-$C_4$ straight or branched alkyl, or Ar-substituted-$C_2$-$C_4$ straight or branched alkenyl or alkynyl; wherein $R_6$ is optionally substituted with up to 3 substituents independently selected from halo, hydroxy, nitro, cyano or amino;

each $R_{12}$ is independently selected from $R_6$, W—[$C_1$-$C_4$ straight or branched alkyl], W—[$C_2$-$C_4$ straight or branched alkenyl or alkynyl], Ar-substituted-[W—[$C_1$-$C_4$ straight or branched alkyl]], Ar-substituted-[W—[$C_2$-$C_4$ straight or branched alkenyl or alkynyl]], O—Ar, N($R_6$)—Ar, S—Ar, S(O)—Ar, S(O)$_2$—Ar, S—C(O)H, N($R_6$)—C(O)H, or O—C(O)H; wherein W is O—, O—C(O)—, S—, S(O)—, S(O)$_2$—, S—C(O)—, N($R_6$)—, or N($R_6$)—C(O)—; and wherein each $R_{12}$ is optionally and independently substituted with up to 3 substituents independently selected from halo, hydroxy, nitro, cyano or amino.

and

Y is selected from —O—, —S—, —C|C—, —C($R_{12}$)$_2$—C($R_{12}$)$_2$—, —C($R_{12}$)$_2$— or —C($R_{12}$)=C($R_{12}$)—; wherein each of $R_1$, $R_2$, $R_3$, $R_4$, $R_5$, $R_7$, $R_8$, $R_9$, $R_{10}$ and $R_{11}$ is independently selected from hydrogen, halo, hydroxy, cyano, nitro, amino, —C(O)NH$_2$, Z-[($C_1$-$C_4$)-straight or branched alkyl], Z-[($C_2$-$C_4$)-straight or branched alkenyl or alkynyl], Ar-substituted-[($C_1$-$C_4$)-straight or branched alkyl], Ar-substituted-[($C_2$-$C_4$)-straight or branched alkenyl or alkynyl], Ar, Q-Ar, [($C_1$-$C_4$)-straight or branched alkyl]-Q-Ar, [($C_2$$C_4$)-straight or branched alkenyl or alkynyl]-QAr, O—[($C_1$-$C_4$)-straight or branched alkyl]-Q-Ar, O—[($C_2$-$C_4$)-straight or branched alkenyl or alkynyl]-Q-Ar, or any two adjacent R groups may be taken together with the carbon atoms to which they are bound to form a 5 to 6-membered aromatic carbocyclic or heterocyclic ring; wherein Z is selected from a bond, O—, S—, —S(O)$_2$—, C(O)—, OC(O)—, or N(H)C(O)—;

Q is selected from O, —O—C(O)—, —C(O)—O—, —N(H)—C(O)—O—, —O—N(H)—C(O)—, —N(H)—C(O)—, —C(O)—N(H)—, —O—C(O)—N(H)—, or —C(O)—N(H)—O—;

Ar is selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl or other chemically feasible monocyclic, bicyclic or tricyclic ring systems, wherein each ring consists of 5 to 7 ring atoms and wherein each ring comprises 0 to 3 heteroatoms independently selected from N, O and S;

$R_{13}$ is selected from [$C_1$-$C_{12}$ straight or branched alkyl] or, [$C_2$-$C_{12}$ straight or branched alkenyl or alkynyl]; wherein $R_{13}$ is optionally substituted with 1 to 4 substituents independently selected from $R_{14}$ or $R_{15}$, wherein each $R_{14}$ is a monocyclic or a bicyclic ring system consisting of 3 to 7 members per ring, wherein said ring system optionally comprises up to 4 heteroatoms selected from N, O, and S; wherein a CH$_2$ adjacent to said N, O or S may be substituted with C(O); and wherein $R_{14}$ optionally comprises up to 2 substituents independently selected from ($C_1$-$C_4$)-straight or branched alkyl, ($C_2$-$C_4$)-straight or branched alkenyl, 1,2-methylenedioxy, 1,2-ethylenedioxy, (CH$_2$)$_n$-$R_{16}$, —S—(CH$_2$)$_n$$R_{16}$, —S(O)—(CH$_2$)$_n$-$R_{16}$, —S(O)$_2$—(CH$_2$)$_n$—$R_{16}$, —O—(CH$_2$)$_n$—$R_{16}$, or —N($R_{18}$)—(CH$_2$)$_n$—$R_{16}$ wherein n is 0, 1 or 2;

$R_{16}$ is selected from halogen, —CN, —NO$_2$, —CF$_3$, —OCF$_3$, —OH, —S—($C_1$-$C_4$)-alkyl, —S(O)—($C_1$-$C_4$)-alkyl, —S(O)$_2$—($C_1$-$C_4$)-alkyl, —NH$_2$, —NH—($C_1$-$C_4$)-alkyl, —N(($C_1$-$C_4$)-alkyl)$_2$, COOH, C(O)—O—($C_1$-$C_4$)-alkyl or O—($C_1$-$C_4$)-alkyl; and each $R_{15}$ is independently selected from —OR$_{17}$, or —N($R_{18}$)$_2$;

$R_{17}$ is selected from hydrogen, —($C_1$-$C_6$)-straight alkyl, —($C_1$-$C_6$)-straight alkyl-Ar, —C(O)—($C_1$-$C_6$)-straight or branched alkyl, —C(O)—Ar, or —($C_1$-$C_6$)-straight alkyl-CN; and each $R_{18}$ is independently selected from —($C_1$-$C_6$)-straight or branched alkyl, —($C_1$-$C_6$)-straight or branched alkyl-Ar, —($C_1$-$C_6$)-straight alkyl-CN, —($C_1$-$C_6$)-straight alkyl-OH, —($C_1$-$C_6$)-straight alkyl-OR$_{17}$, —C(O)—($C_1$-$C_6$)-straight or branched alkyl, —C(O)—Ar, —S(O)$_2$—($C_1$-$C_6$)-straight or branched alkyl, or —S(O)$_2$—Ar; wherein any alkyl, alkenyl or alkynyl group is optionally substituted with 1 to 3 independently selected halo groups; and any Ar, aromatic carbocyclic ring or heterocyclic ring is optionally substituted with 1 to 3 substituents independently selected from halo, hydroxy, nitro, cyano, amino, ($C_1$-$C_4$)-straight or branched alkyl; O—($C_1$-$C_4$)-straight or branched alkyl, ($C_2$-$C_4$)-straight or branched alkenyl or alkynyl, or O—($C_2$-$C_4$)-straight or branched alkenyl or alkynyl; and any Ar, aromatic carbocyclic ring or heterocyclic ring is optionally benzofused.

In addition, in these compounds, at least two of $R_1$, $R_2$, $R_3$, $R_4$, or $R_5$ is hydrogen;

no more than two of $R_1$, $R_2$, $R_3$, $R_4$, or $R_5$ comprises Ar;

at least two of $R_7$, $R_8$, $R_9$, $R_{10}$ or $R_{11}$ is hydrogen; and no more than two of $R_7$, $R_8$, $R_9$, $R_{10}$ or $R_{11}$ comprises Ar.

The compounds of this invention specifically exclude those wherein X is —NH—S(O)$_2$— or —S(O)$_2$—N(H)—, one of $R_1$, $R_2$, $R_3$, $R_4$, $R_5$, $R_7$, $R_8$, $R_9$, $R_{10}$ or $R_{11}$ is O—($C_1$-$C_4$)-straight or branched alkyl, seven of $R_1$, $R_2$, $R_3$, $R_4$, $R_5$, $R_7$, $R_8$, $R_9$, $R_{10}$ or $R_{11}$ is hydrogen and the remaining two of $R_1$, $R_2$, $R_3$, $R_4$, $R_5$, $R_7$, $R_8$, $R_9$, $R_{10}$ or $R_{11}$ are bound together to form a 5 to 6-membered aromatic carbocyclic or heterocyclic ring, Also excluded are compounds wherein X is —NH—S(O)$_2$— or —S(O)$_2$—N(H)—, two of $R_1$, $R_2$, $R_3$, $R_4$, $R_5$, $R_7$, $R_8$, $R_9$, $R_{10}$ or $R_{11}$ are O—($C_1$-$C_4$)-straight or branched alkyl, seven of $R_1$, $R_2$, $R_3$, $R_4$, $R_5$, $R_7$, $R_8$, $R_9$, $R_{10}$ or $R_{11}$ is hydrogen and the remaining one of $R_1$, $R_2$, $R_3$, $R_4$, $R_5$, $R_7$, $R_8$, $R_9$, $R_{10}$ or $R_{11}$ is —NO$_2$, —CN or —Ar.

Another set of compounds excluded from the present invention are those wherein X is —NH—S(O)$_2$— or —S(O)$_2$—N(H)—, two of $R_1$, $R_2$, $R_3$, $R_4$, $R_5$, $R_7$, $R_8$, $R_9$, $R_{10}$ or $R_{11}$ are O—(C$_1$-C$_4$)-straight or branched alkyl, six of $R_1$, $R_2$, $R_3$, $R_4$, $R_5$, $R_7$, $R_8$, $R_9$, $R_{10}$ or $R_{11}$ is hydrogen and the remaining two of $R_1$, $R_2$, $R_3$, $R_4$, $R_5$, $R_7$, $R_8$, $R_9$, $R_{10}$ or $R_{11}$ are both halo.

Yet another set of compounds excluded are those wherein X is —NH—S(O)$_2$— or —S(O)$_2$—N(H)—, one of $R_1$, $R_2$, $R_3$, $R_4$, $R_5$, $R_7$, $R_8$, $R_9$, $R_{10}$ or $R_{11}$ is Ar and the remaining 9 of $R_1$, $R_2$, $R_3$, $R_4$, $R_5$, $R_7$, $R_8$, $R_9$, $R_{10}$ or $R_{11}$ are each hydrogen.

Another set of excluded compounds are those wherein X is —N(H)—C(O)—S— or —S—C(O)—N(H)—, one of $R_1$, $R_2$, $R_3$, $R_4$, $R_5$, $R_7$, $R_8$, $R_9$, $R_{10}$ or $R_{11}$ is —OH, eight of $R_1$, $R_2$, $R_3$, $R_4$, $R_5$, $R_7$, $R_8$, $R_9$, $R_{10}$ or $R_{11}$ are hydrogen and the remaining one of $R_1$, $R_2$, $R_3$, $R_4$, $R_5$, $R_7$, $R_8$, $R_9$, $R_{10}$ or $R_{11}$ is halo; and those wherein X is —N(H)—C(O)—S— or —S—C(O)—N(H)—, one of $R_1$, $R_2$, $R_3$, $R_4$, $R_5$, $R_7$, $R_8$, $R_9$, $R_{10}$ or $R_{11}$ is —OH, seven of $R_1$, $R_2$, $R_3$, $R_4$, $R_5$, $R_7$, $R_8$, $R_9$, $R_{10}$ or $R_{11}$ are hydrogen, one of $R_1$, $R_2$, $R_3$, $R_4$, $R_5$, $R_7$, $R_8$, $R_9$, $R_{10}$ or $R_{11}$ is O—(C$_1$-C$_4$)-straight or branched alkyl and the remaining one of $R_1$, $R_2$, $R_3$, $R_4$, $R_5$, $R_7$, $R_8$, $R_9$, $R_{10}$ or $R_{11}$ is halo or (C$_1$C$_4$)-straight or branched alkyl.

Finally, another set of excluded compounds are those wherein, when X is —C(O)—N(R$_6$)— or —N(R$_6$)—C(O)—, two adjacent groups selected from either $R_1$, $R_2$, $R_3$, $R_4$ and $R_5$, or from $R_7$, $R_8$, $R_9$, $R_{10}$ and $R_{11}$ may not be taken together with the carbon atoms to which they are bound to form a 6-membered aromatic carbocyclic ring.

The above-described exclusions from the compounds of this invention reflect compounds which are commercially available. However, those compounds are not known or suggested to inhibit IMPDH, nor have they ever been know or suggested to be formulated with a pharmaceutically acceptable adjuvant, carrier or excipient. Accordingly, these compounds are not excluded from aspects of this invention which involve any methods or compositions recited below.

The term "heterocyclic ring" as used herein refers to a ring which comprises 1 to 4 heteroatoms independently selected from N, O or S.

The terms "Ar-substituted-(C$_1$-C$_4$)-straight or branched alkyl" and "Ar-substituted-(C$_2$-C$_4$)-straight or branched alkenyl or alkynyl" denote that one or more Ar groups may be attached to the alkyl, alkenyl or alkynyl chain at any chemically feasible position on the chain, including the termini.

References to "[branched alkyl, alkenyl or alkynyl]-Ar" or "[branched alkyl, alkenyl or alkynyl]-Q-Ar" denote that an "Ar" or "Q-Ar" moiety is attached to one or more terminal ends of the branched alkyl, alkenyl or alkynyl chain.

According to a preferred embodiment X is selected from —C(O)—N(R$_6$)—, —N(R$_6$)—C(O)—, —CH$_2$—N(R$_6$)—, or —N(R$_6$)—CH$_2$— or —N(R$_6$)—C(O)—Y. More preferably, X is —N(R$_6$)—C(O)—Y. Most preferably X is —N(R$_6$)—C(O)—C(R$_{12}$)=C(R$_{12}$)—.

According to another preferred embodiment, $R_1$ is selected from H, (C$_1$-C$_4$)-straight or branched alkyl, OH, O—(C$_1$-C$_4$)-straight or branched alkyl, O—Ar, OCF$_3$, halo, cyano or S—(C$_1$-C$_4$)-straight or branched alkyl. In an alternate preferred embodiment, $R_1$ is H when $R_2$ is not H.

$R_2$ is preferably selected from H, (C$_1$-C$_4$)-straight or branched alkyl, Ar, O—(C$_1$-C$_4$)-straight or branched alkyl, O—Ar, OCF$_3$, halo, cyano, C(O)NH$_2$ or S(O)$_2$—(C$_1$-C$_4$)-straight or branched alkyl. More preferably, $R_2$ is H.

$R_3$ is preferably selected from H, Ar, cyano, O—(C$_1$-C$_4$)-straight or branched alkyl, O—Ar, S—(C$_1$-C$_4$)-straight or branched alkyl, CF$_3$ or OCF$_3$.

In another preferred embodiment, $R_4$ is selected from H, (C$_1$-C$_4$)-straight or branched alkyl, OH, O—(C$_1$-C$_4$)-straight or branched alkyl, O—Ar, OCF$_3$, halo, cyano or S—(C$_1$-C$_4$)-straight or branched alkyl.

$R_5$ is preferably selected from H, (C$_1$-C$_4$)-straight or branched alkyl, Ar, O—(C$_1$-C$_4$)-straight or branched alkyl, O—Ar, OCF$_3$, halo, cyano, C(O)NH$_2$ or S(O)$_2$—(C$_1$-C$_4$)-straight or branched alkyl. More preferably, $R_5$ is H.

According to another preferred embodiment, $R_7$ is selected from H, OH, CO(O)—(C$_1$-C$_4$)-straight or branched alkyl, O—(C$_1$-C$_4$)-straight or branched alkyl, O—Ar, amino, or N(H)C(O)—(C$_1$-C$_4$)-straight or branched alkyl. Even more preferred is when $R_7$ is OH.

$R_8$ is preferably H, (C$_1$-C$_4$)-straight or branched alkyl, O—(C$_1$-C$_4$)-straight or branched alkyl, or (C$_1$-C$_4$)-straight or branched alkyl-N(H)C(O)O—Ar.

According to another preferred embodiment, $R_9$ is selected from H, (C$_1$-C$_4$)-straight or branched alkyl, O—(C$_1$-C$_4$)-straight or branched alkyl, or $R_9$ is taken together with $R_{10}$ and the carbon atoms to which they are bound to form a fused benzene ring. More preferred is when $R_9$ and $R_{10}$ are taken together with the carbon atoms to which they are bound to form a fused benzene ring.

According to a further preferred embodiment, $R_{10}$ is selected from H, (C$_1$-C$_4$)-straight or branched alkyl, O—(C$_1$-C$_4$)-straight or branched alkyl, or $R_{10}$ is taken together with $R_9$ and the carbon atoms to which they are bound to form a fused benzene ring.

In another preferred embodiment, $R_{11}$ is selected from H, OH, OC(O)—(C$_1$-C$_4$)-straight or branched alkyl, O—(C$_1$-C$_4$)-straight or branched alkyl, O—Ar, amino, or N(H)C(O)—(C$_1$-C$_4$)-straight or branched alkyl. More preferably, $R_{11}$ is H.

According to another embodiment, preferred compounds of the invention are listed in the table below.

TABLE 1

Preferred compounds.

| Cmpd | Molecular Structure |
|---|---|
| 100 | 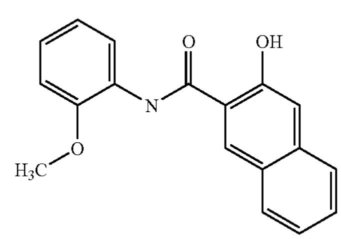 |

TABLE 1-continued
Preferred compounds.
| Cmpd | Molecular Structure |
|------|---------------------|
| 101 | 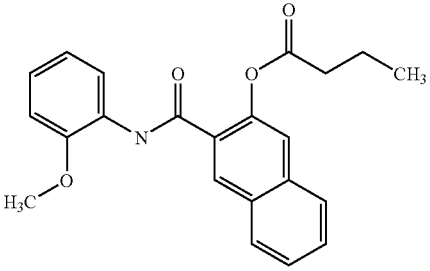 |
| 102 | 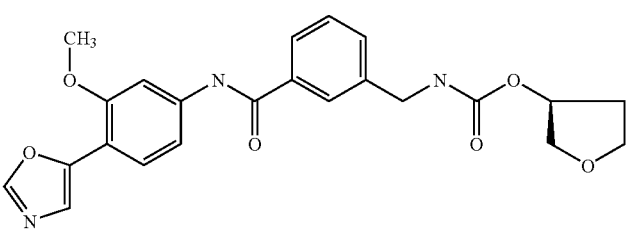 |
| 103 | 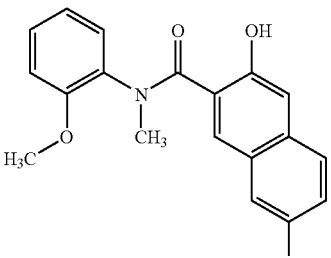 |
| 104 | 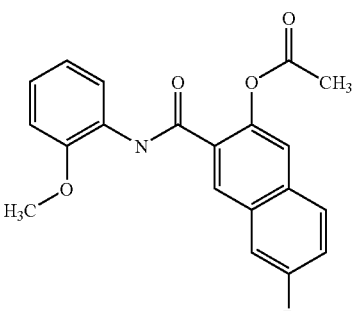 |
| 105 | 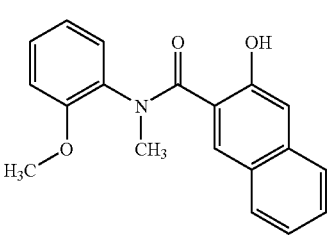 |

TABLE 1-continued

Preferred compounds.

| Cmpd | Molecular Structure |
|------|---------------------|
| 106 | 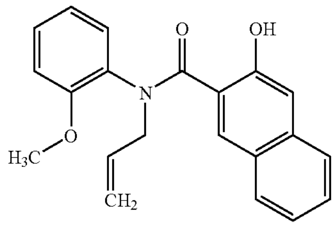 |
| 107 | 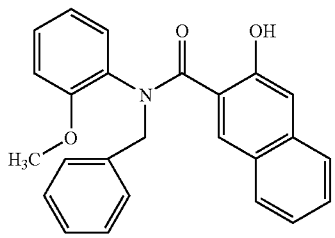 |
| 108 | 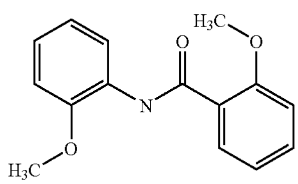 |
| 109 | 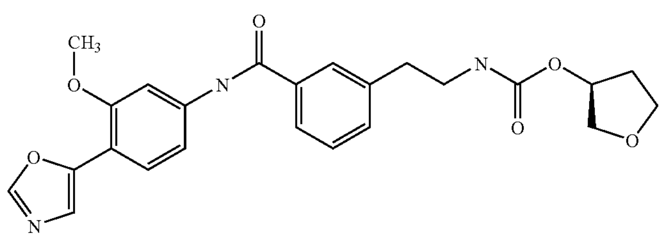 |
| 110 | 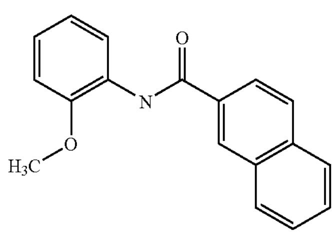 |
| 111 | 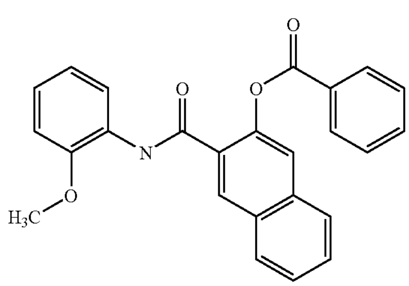 |

TABLE 1-continued

Preferred compounds.

| Cmpd | Molecular Structure |
|------|---------------------|
| 112  | 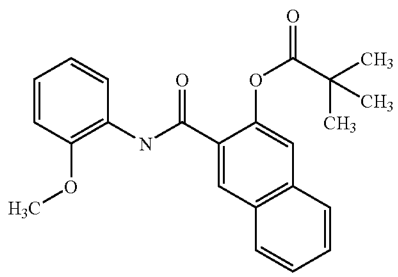                    |
| 113  | 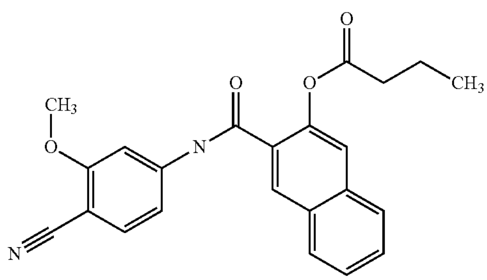                    |
| 114  | 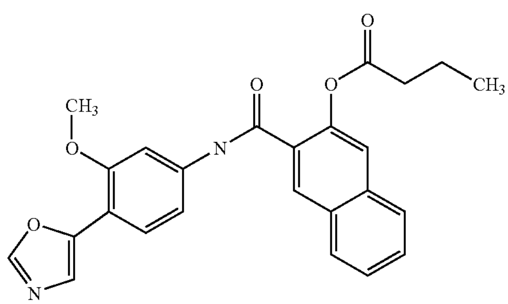                    |
| 115  | 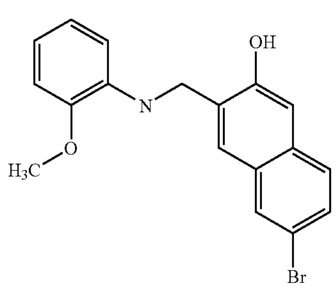                    |
| 116  | 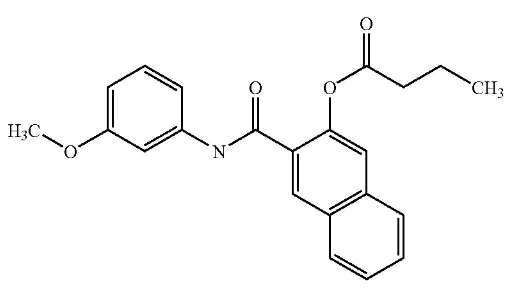                    |

TABLE 1-continued

Preferred compounds.

| Cmpd | Molecular Structure |
|---|---|
| 117 | 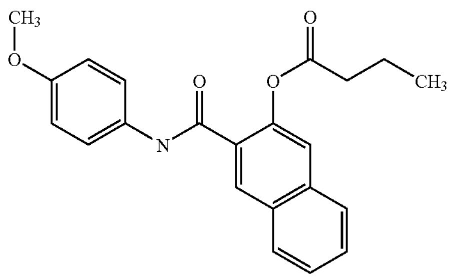 |
| 118 | 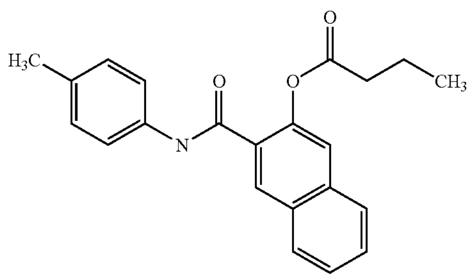 |
| 119 | 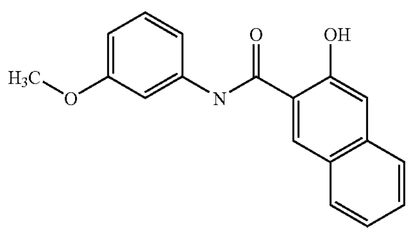 |
| 120 | 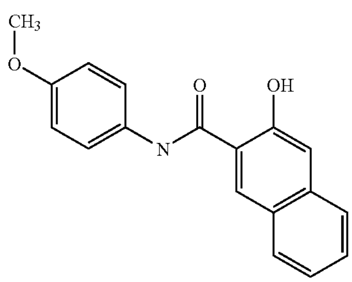 |
| 121 | 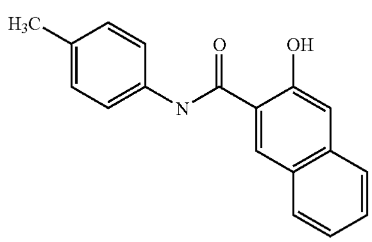 |
| 122 | 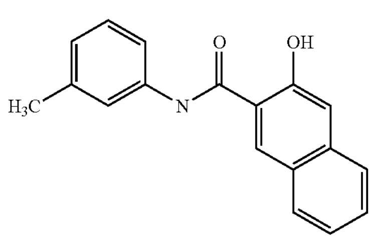 |

TABLE 1-continued

Preferred compounds.

| Cmpd | Molecular Structure |
|------|---------------------|
| 123  | 3-hydroxy-N-(3-(trifluoromethyl)phenyl)-2-naphthamide |
| 124  | 3-hydroxy-N-(4-(trifluoromethyl)phenyl)-2-naphthamide |
| 125  | N-(4-cyano-3-methoxyphenyl)-3-hydroxy-2-naphthamide |
| 126  | 3-hydroxy-N-(3-methoxy-4-(oxazol-5-yl)phenyl)-2-naphthamide |
| 127  | 6-bromo-3-((2-methoxyphenyl)carbamoyl)naphthalen-2-yl propionate |
| 128  | 3-hydroxy-N-(2-(trifluoromethyl)phenyl)-2-naphthamide |

TABLE 1-continued

Preferred compounds.

| Cmpd | Molecular Structure |
|------|---------------------|
| 129  | N-(2-bromophenyl)-3-hydroxy-2-naphthamide |
| 130  | N-(3-bromophenyl)-3-hydroxy-2-naphthamide |
| 131  | N-(4-bromophenyl)-3-hydroxy-2-naphthamide |
| 132  | 3-hydroxy-N-(2-methylphenyl)-2-naphthamide |
| 133  | N-(2-methoxyphenyl)benzamide |
| 134  | N-(2-methoxyphenyl)-1,3-benzodioxole-5-carboxamide |

TABLE 1-continued
Preferred compounds.
| Cmpd | Molecular Structure |
|------|---------------------|
| 135  | 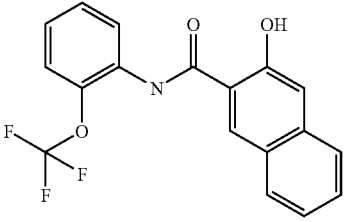 |
| 136  | 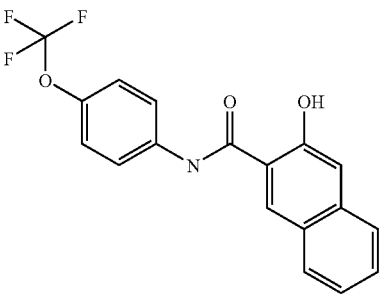 |
| 137  | 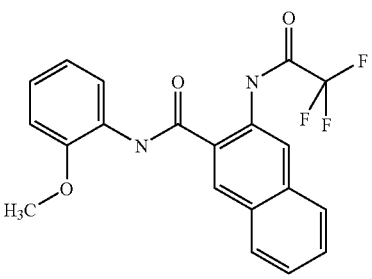 |
| 138  | 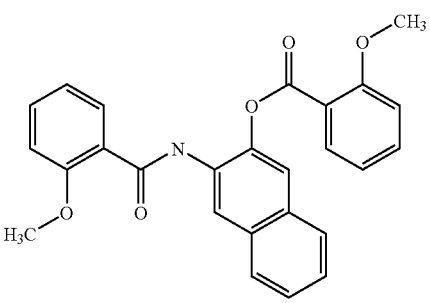 |
| 139  | 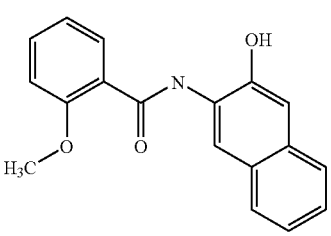 |

TABLE 1-continued

Preferred compounds.

| Cmpd | Molecular Structure |
|------|---------------------|
| 140  | 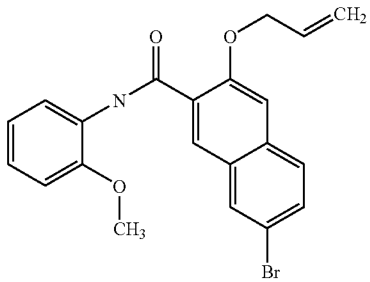 |
| 141  | 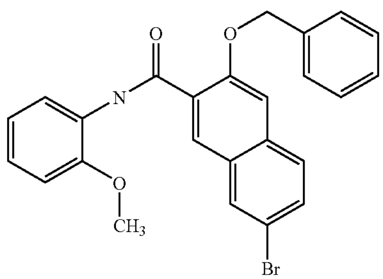 |
| 142  | 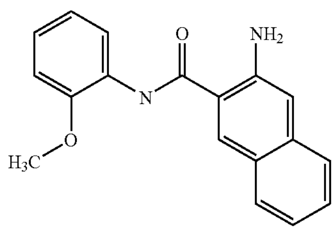 |
| 143  | 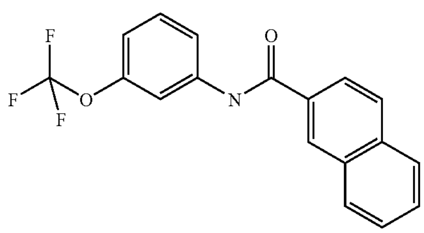 |
| 144  | 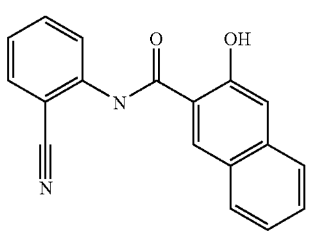 |
| 145  | 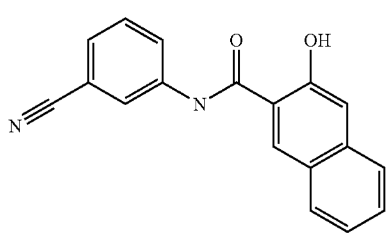 |

TABLE 1-continued
Preferred compounds.
| Cmpd | Molecular Structure |
|---|---|
| 146 | 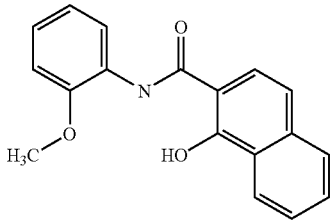 |
| 147 | 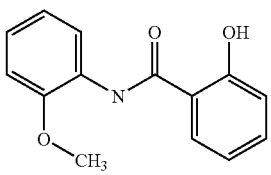 |
| 148 | 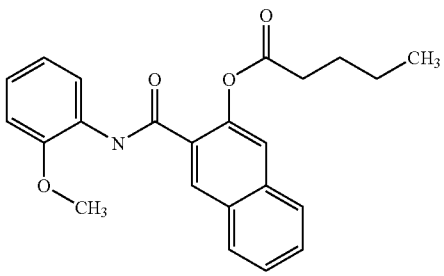 |
| 149 | 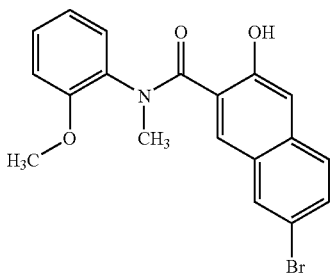 |
| 150 | 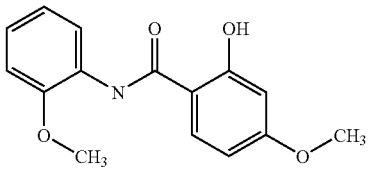 |
| 151 | 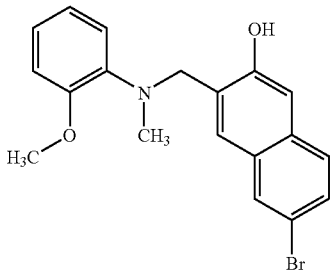 |

TABLE 1-continued

Preferred compounds.

| Cmpd | Molecular Structure |
|------|---------------------|
| 152  | 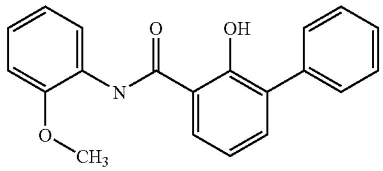 |
| 153  | 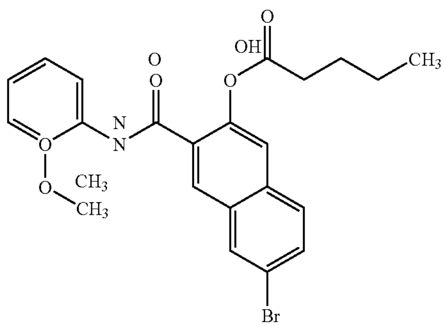 |
| 154  | 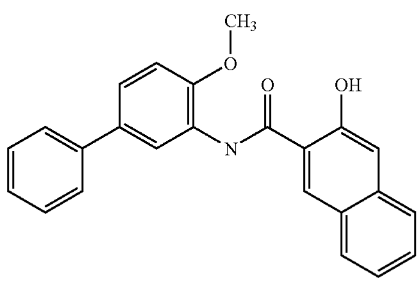 |
| 155  | 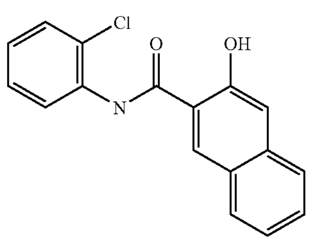 |
| 156  | 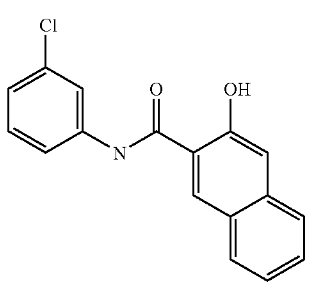 |
| 157  | 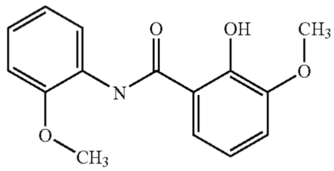 |

TABLE 1-continued

Preferred compounds.

| Cmpd | Molecular Structure |
| --- | --- |
| 159 | [Structure: 5-(ethylsulfonyl)-2-methoxyphenyl derivative of N-aryl-3-hydroxy-2-naphthamide] |
| 160 | [Structure: 5-(difluoromethylsulfonyl)-2-methoxyphenyl derivative of N-aryl-3-hydroxy-2-naphthamide] |
| 161 | [Structure: N-(4-chlorophenyl)-3-hydroxy-2-naphthamide] |
| 162 | [Structure: N-(2-fluorophenyl)-3-hydroxy-2-naphthamide] |
| 163 | [Structure: N-(3-fluorophenyl)-3-hydroxy-2-naphthamide] |

TABLE 1-continued

Preferred compounds.

| Cmpd | Molecular Structure |
| --- | --- |
| 164 | 5-sec-butyl-2-methoxyphenyl 3-hydroxy-2-naphthamide |
| 165 | 5-carbamoyl-2-methoxyphenyl 3-hydroxy-2-naphthamide |
| 166 | 4-fluorophenyl 3-hydroxy-2-naphthamide |
| 167 | 2-ethoxyphenyl 3-hydroxy-2-naphthamide |
| 168 | 3-ethoxyphenyl 3-hydroxy-2-naphthamide |

TABLE 1-continued

Preferred compounds.

| Cmpd | Molecular Structure |
|---|---|
| 169 | N-(2-(methylthio)phenyl)-3-hydroxy-2-naphthamide |
| 170 | N-(4-chloro-2,5-dimethoxyphenyl)-3-hydroxy-2-naphthamide |
| 171 | N-(5-chloro-2,4-dimethoxyphenyl)-3-hydroxy-2-naphthamide |
| 172 | N-(7-methoxydibenzofuran-3-yl)-3-hydroxy-2-naphthamide |
| 173 | N-(3-(methylthio)phenyl)-3-hydroxy-2-naphthamide |
| 174 | N-(2-methoxyphenyl)-2-hydroxy-4-methoxybenzamide |

TABLE 1-continued
Preferred compounds.
| Cmpd | Molecular Structure |
|---|---|
| 175 | 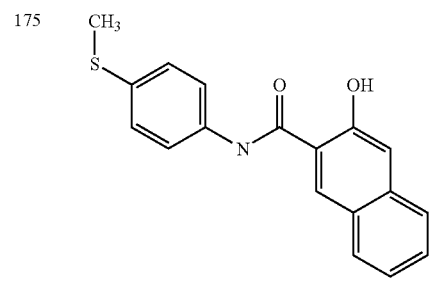 |
| 177 | 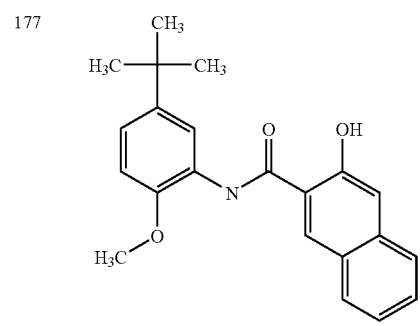 |
| 178 | 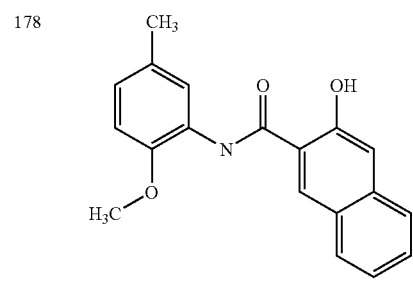 |
| 179 | 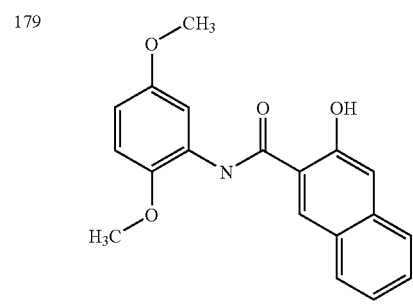 |
| 180 | 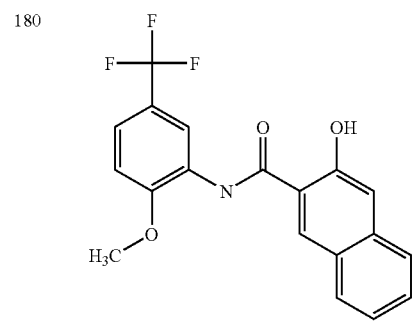 |

TABLE 1-continued

Preferred compounds.

| Cmpd | Molecular Structure |
|------|---------------------|
| 181 | 4-chloro-2-methoxy-5-methylphenyl 3-hydroxy-2-naphthamide |
| 182 | 3-methoxy-4-(oxazol-5-yl)phenyl 3-hydroxy-2-naphthamide |
| 183 | 2-phenoxyphenyl 3-hydroxy-2-naphthamide |
| 184 | 2,3-dimethoxyphenyl 3-hydroxy-2-naphthamide |
| 185 | 4-phenoxyphenyl 3-hydroxy-2-naphthamide |

TABLE 1-continued
Preferred compounds.
| Cmpd | Molecular Structure |
|------|---------------------|
| 186  | 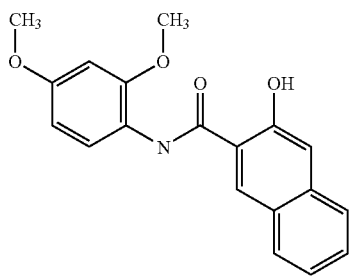 |
| 187  | 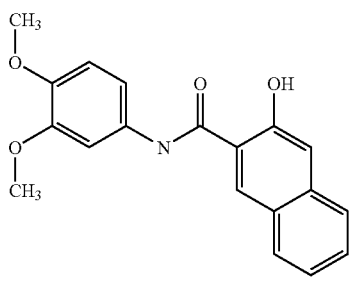 |
| 188  | 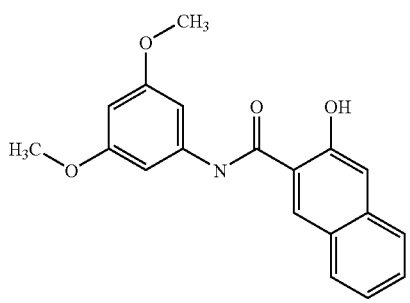 |
| 190  | 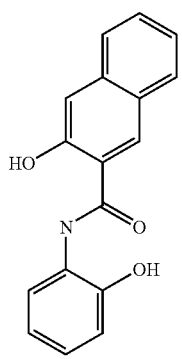 |

TABLE 1-continued
Preferred compounds.
| Cmpd | Molecular Structure |
|------|---------------------|
| 191  | 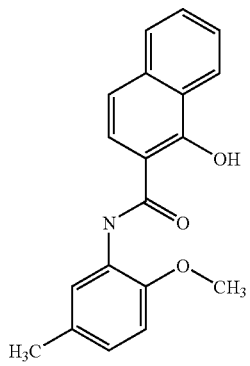 |
| 192  | 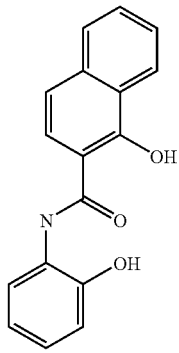 |
| 193  | 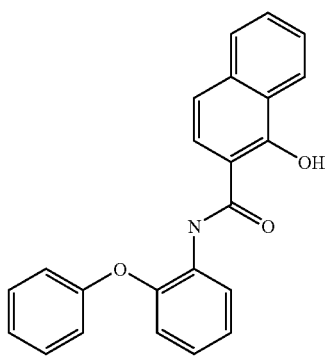 |
| 194  | 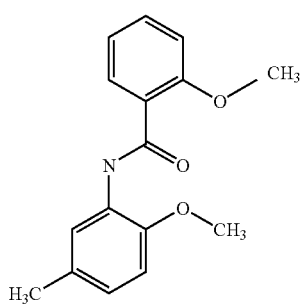 |

TABLE 1-continued
Preferred compounds.
| Cmpd | Molecular Structure |
|------|---------------------|
| 195 | 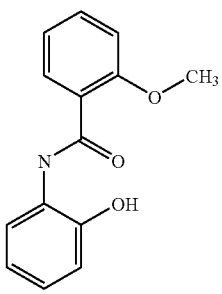 |
| 196 | 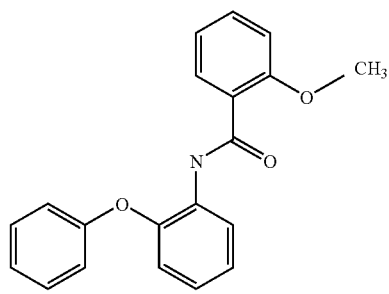 |
| 197 | 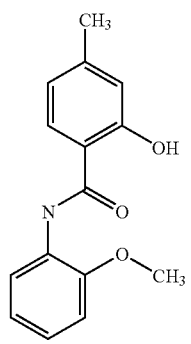 |
| 198 | 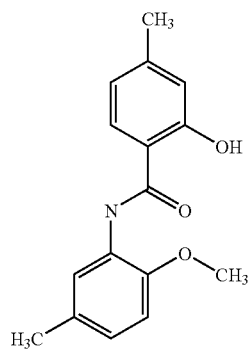 |

TABLE 1-continued
Preferred compounds.
Cmpd | Molecular Structure
199
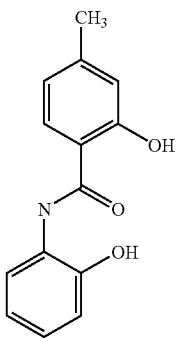
200
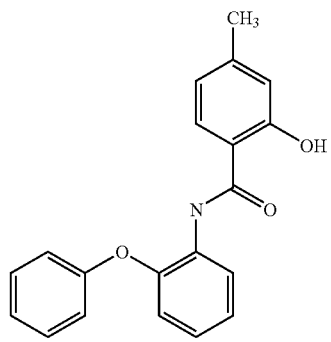
201
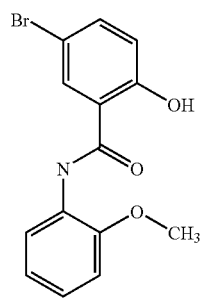
202
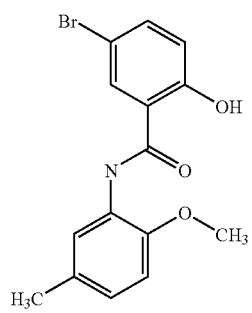

TABLE 1-continued
Preferred compounds.
| Cmpd | Molecular Structure |
|------|---------------------|
| 203 | 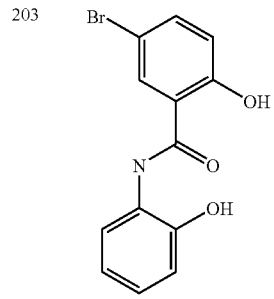 |
| 204 | 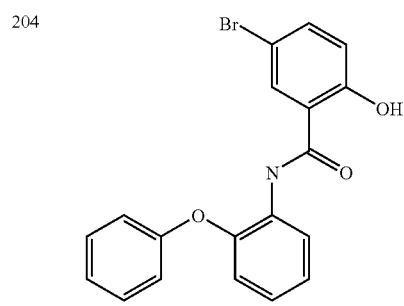 |
| 300 | 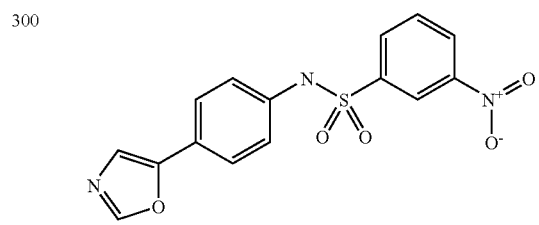 |
| 301 | 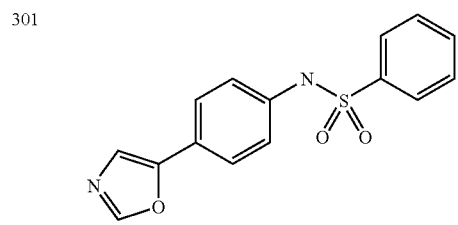 |
| 302 | 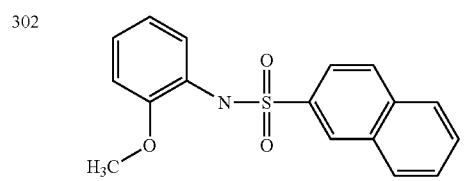 |
| 303 | 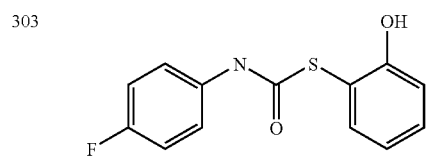 |

TABLE 1-continued

Preferred compounds.

| Cmpd | Molecular Structure |
|------|---------------------|
| 304  | 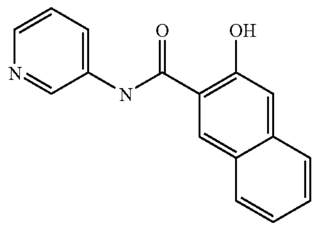                    |
| 305  | 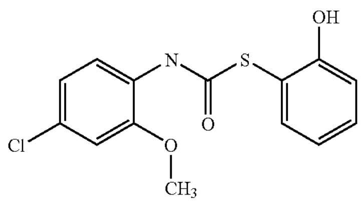                    |
| 306  | 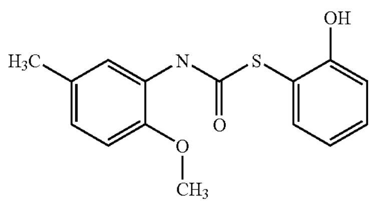                    |
| 307  | 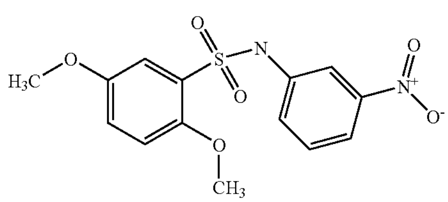                    |
| 308  | 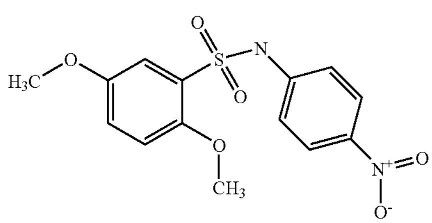                    |
| 309  | 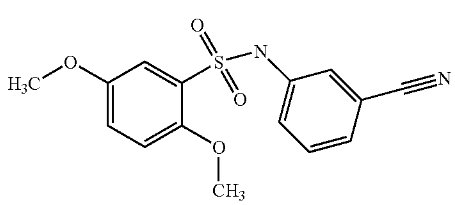                    |
| 310  | 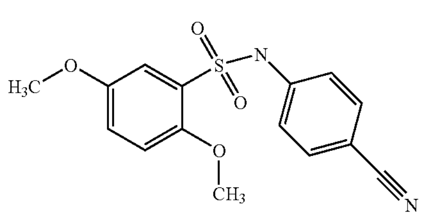                    |

TABLE 1-continued

Preferred compounds.

| Cmpd | Molecular Structure |
|---|---|
| 311 | 2,6-dimethoxy-N-(4-tert-butylphenyl)benzenesulfonamide |
| 312 | N-(2-cyanophenyl)-2,5-dimethoxybenzenesulfonamide |
| 313 | N-(3-bromophenyl)-2,5-dimethoxybenzenesulfonamide |
| 314 | N-(2-chloro-6-fluorobenzyl)-2,5-dimethoxybenzenesulfonamide |
| 315 | N-(2-chlorophenyl)-2,5-dimethoxybenzenesulfonamide |
| 316 | 2,5-dimethoxy-N-(4-(1,2,4-oxadiazol-3-yl)phenyl)benzenesulfonamide |

TABLE 1-continued
Preferred compounds.
| Cmpd | Molecular Structure |
|---|---|
| 317 | 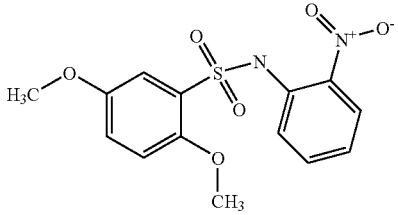 |
| 318 | 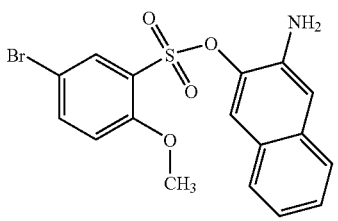 |
| 319 | 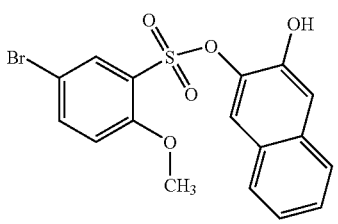 |
| 320 | 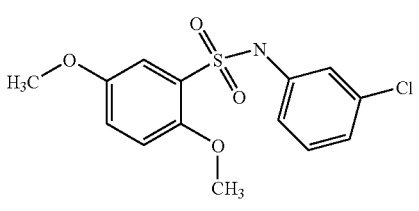 |
| 321 | 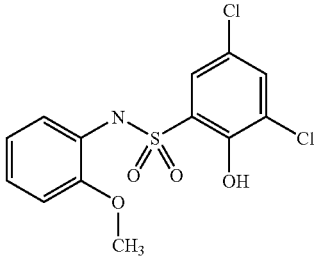 |
| 322 | 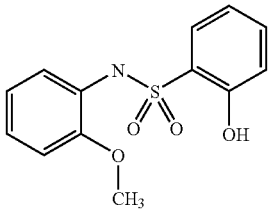 |

TABLE 1-continued

Preferred compounds.

| Cmpd | Molecular Structure |
|---|---|
| 323 | [Structure: 5-bromo-2-methoxyphenyl sulfonate ester of 2-hydroxyphenol] |
| 324 | [Structure: 2-methoxybenzenesulfonamide of 2-hydroxyaniline] |
| 325 | [Structure: 3-methoxy-4-(oxazol-5-yl)phenyl amide with benzyl carbamate of (S)-tetrahydrofuran-3-ol] |
| 326 | [Structure: 3-methoxy-4-(oxazol-5-yl)phenyl carbamate with benzyl carbamate of (S)-tetrahydrofuran-3-ol] |

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

As used herein, the compounds of this invention, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of the compounds of this invention.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of this invention may be synthesized using conventional techniques. Advantageously, these compounds are conveniently synthesized from readily available starting materials.

In general, compounds of this invention are conveniently obtained via methods illustrated in Scheme 1 below:

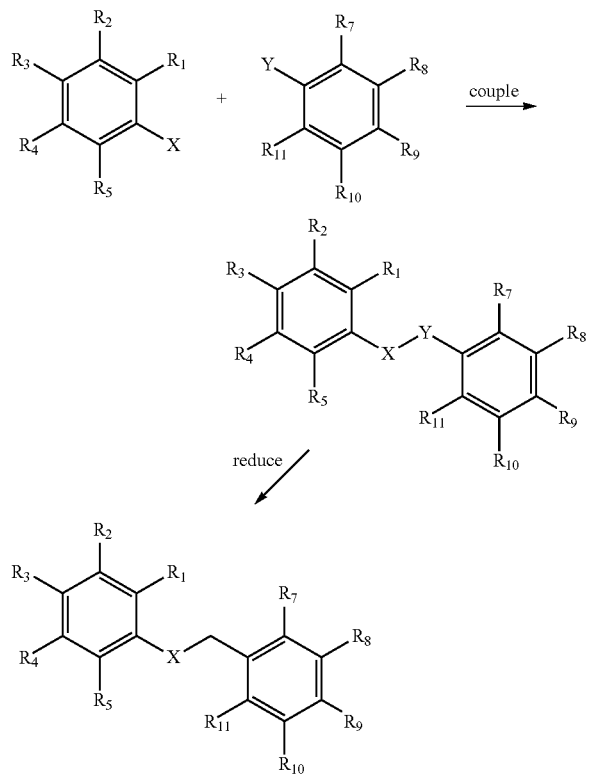

The coupling step indicated in Scheme 1 was used to produce the benzamide, arylacetamide, sulfonamide, carbamate and thiocarbamate compounds of this invention.

Materials used for coupling and reduction are indicated below:

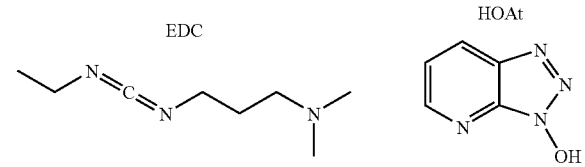

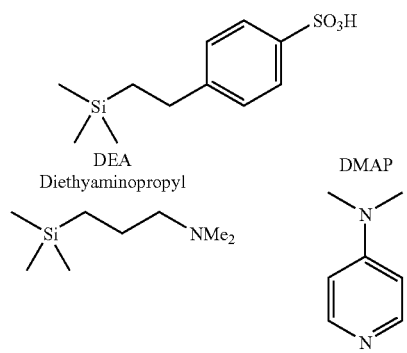

TEA = Et$_3$N

For benzamide synthesis, A in the initial step was —N(H)R$_6$ and B was —C(O)OH or —C(O)Cl. The coupling was performed in the presence of EDC, HOAt and CH$_3$CN.

For arylacetamide synthesis, A in the initial step was —N(H)R$_6$ and B was —Y—C(O)OH or —Y—C(O)Cl. The coupling was performed in the presence of EDC, CH$_2$Cl$_2$ and DMAP.

For sulfonamide synthesis, A in the initial step was N(H)R$_6$ and B was S(O)$_2$Cl. The coupling was performed in the presence of TEA and CH$_2$Cl$_2$.

For carbamate synthesis, A in the initial step was N(H)R$_6$ and B was OC(O)Cl. The coupling was performed in the presence of TEA and CH$_2$Cl$_2$.

For thiocarbamate synthesis, A in the initial step was NC(O) and B was SH. The coupling was performed in the presence of DMAP and CH$_2$Cl$_2$.

The reduction step indicated in scheme 1 was used to produce the benzyl amines of this invention. In the coupled molecule A'-B' was N(R$_6$)—C(O) and reduction was carried out in the presence of BH$_3$.THF/THF.

The above reactions were carried out at room temperature for 5 hours with constant shaking.

Once synthesized, compounds were purified by solid phase extraction (SPE) on a bed of Varian DEA and Varian SCX sorbents in a 2:1 ratio (w/w): 180 mg was packed into 1 mL cartridges.

The procedure is as follows:

| Event | Volume | Flow rate |
|---|---|---|
| condition sorbent | 1.5 ml | 3 mL/min |
| load and collect | 0.9 ml | 3 mL/min |
| elute | 1.5 ml | 1 mL/min |

The collected solution contained product at >95% purity (HPLC: 210 nm) with traces of O-acylated impurity. Yields were typically 8-12 mg.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for IMPDH. Accordingly, these compounds are capable of targeting and inhibiting IMPDH enzyme. Inhibition can be measured by various methods, including, for example, IMP dehydrogenase HPLC-assays (measuring enzymatic production of XMP and NADH from IMP and NAD) and IMP dehydrogenase spectrophotometric assays (measuring enzymatic production of NADH from NAD). [See C. Montero et al., *Clinica Chimica Acta,* 238, pp. 169-178 (1995)].

Compositions of this invention comprise a compound of this invention or a salt thereof; an additional agent selected from an immunosuppressant, an anti-cancer agent, an antiviral agent, anti-inflammatory agent, antifungal agent, antibiotic, or an anti-vascular hyperproliferation compound; and any pharmaceutically acceptable carrier, adjuvant or vehicle. Alternate compositions of this invention comprise a compound of this invention or a salt thereof; and a pharmaceutically acceptable carrier, adjuvant or vehicle. Such composition may optionally comprise an additional agent selected from an immunosuppressant, an anti-cancer agent, an antiviral agent, anti-inflammatory agent, antifungal agent, antibiotic, or an anti-vascular hyperproliferation compound. Preferably, the compositions of this invention are pharmaceutical compositions.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of this invention.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, *Ph. Helv.*, or a similar alcohol, or carboxymethyl cellulose or similar dispersing agents which are commonly used in the formulation of pharmaceutically acceptable dosage forms such as emulsions and or suspensions Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the IMPDH inhibitory compounds described herein are useful in a monotherapy and/or in combination therapy for the prevention and treatment of IMPDH mediated disease. Typically, the pharmaceutical compositions of this invention will be administered from about 1 to about 5 times per day or alternatively as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprises a combination of an IMPDH inhibitor of this invention and one or more additional therapeutic or prophylactic agents, both the IMPDH inhibitor and the additional agent should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon and mizoribine.

According to an alternate embodiment, the pharmaceutical compositions of this invention may additionally comprise an anti-cancer agent. Examples of anti-cancer agents include, but are not limited to, cisplatin, actinomycin D, doxorubicin, vincristine, vinblastine etoposide, amsacrine, mitoxantrone, tenipaside, taxol, colchicine, cyclosporin A, phenothiazines, interferon and thioxantheres.

According to another alternate embodiment, the pharmaceutical compositions of this invention may additionally comprise an anti-viral agent. Examples of anti-viral agents include, but are not limited to, Cytovene, Ganciclovir, trisodium phosphonoformate, Ribavirin, d4T, ddI, AZT, and acyclovir.

According to yet another alternate embodiment, the pharmaceutical compositions of this invention may additionally comprise an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In an alternate embodiment, this invention provides methods of treating or preventing IMPDH mediated disease in a mammal comprising the step of administrating to said mammal any of the pharmaceutical compositions and combinations described above. If the pharmaceutical composition only comprises the IMPDH inhibitor of this invention as the active component, such methods may additionally comprise the step of administering to said mammal an agent selected from-an anti-inflammatory agent, immunosuppressant, an anti-cancer agent, an anti-viral agent, or an anti-vascular hyperproliferation compound. Such additional agent may be administered to the mammal prior to, concurrently with, or following the administration of the IMPDH inhibitor composition.

In a preferred embodiment, these methods are useful in suppressing an immune response in a mammal. Such methods are useful in treating or preventing diseases, including, transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitus), lupus, diabetes, mellitus myasthenia gravis, psoriasis, dermatitis, eczema, seborrhea, pulmonary inflammation, eye uveitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

These methods comprise the step of administering to the mammal a composition comprising a compound of this invention and a pharmaceutically acceptable adjuvant. In a preferred embodiment, this particular method comprises the additional step of administering to said mammal a composition comprising an additional immunosuppressant and a pharmaceutically acceptable adjuvant.

Alternatively, this method comprises the step of administering to said mammal a composition comprising a compound of this invention; an additional immunosuppressive agent and a pharmaceutically acceptable adjuvant.

In an alternate preferred embodiment, these methods are useful for inhibiting viral replication in a mammal. Such methods are useful in treating or preventing DNA and RNA viral diseases caused by infection for example, by orthomyxoviruses (influenza viruses types A and B), paramyxoviruses (respiratory syncytial virus (RSV), subacute sclerosing panencephalitis (SSPE) virus) measles and parainfluenza type 3), herpes viruses (HSV-1, HSV-2, HHV-6, HHV-7, HHV-8, Epstein Barr Virus (EBV), cytomegalovirus (HCMV) and varicella zoster virus (VZV)), retroviruses (HIV-1, HIV-2, HTLV-1, HTLV-2), flavi- and pestiviruses (yellow fever virus (YFV), hepatitis C virus (HCV), dengue fever virus, bovine viral diarrhea virus (BVDV), hepatotrophic viruses (hepatitis A virus (HAV), hepatitis B virus (HBV), HCV, hepatitis D virus (HDV), hepatitis E virus (HEV), hepatitis G virus (HGV), Crimean-Congo hemorrhagic fever virus (CCHF), bunyaviruses (Punta Toro virus, Rift Valley fever virus (RVFV), and sandfly fever Sicilian virus), Hantaan virus, Caraparu virus), human papilloma viruses, encephalitis viruses (La Crosse virus), arena viruses (Junin and Tacaribe virus), reovirus, vesicular stomatitis virus, rhinbviruses, enteroviruses (polio virus, coxsackie viruses, encephalomyocarditis virus (EMC)), Lassa fever virus, and togaviruses (Sindbis and Semlike forest viruses) and poxviruses (vaccinia virus), adenoviruses, rubiola, and rubella.

These methods comprise the step of administering to the mammal a composition comprising a compound of this invention, and a pharmaceutically acceptable adjuvant. In a preferred embodiment, this particular method comprises the additional step of administering to said mammal a composition comprising an additional anti-viral agent and a pharmaceutically acceptable adjuvant.

Alternatively, this method comprises the step of administering to said mammal a composition comprising a compound of this invention, an additional anti-viral agent and a pharmaceutically acceptable adjuvant.

In another alternate preferred embodiment, these methods are useful for inhibiting vascular cellular hyperproliferation in a mammal. Such methods are useful in treating or preventing diseases, including, restenosis, stenosis, artherosclerosis and other hyperproliferative vascular disease.

These methods comprise the step of administering to the mammal a composition comprising a compound of this invention, and a pharmaceutically acceptable adjuvant. In a preferred embodiment, this particular method comprises the additional step of administering to said mammal a composition comprising an additional anti-vascular hyperproliferative agent and a pharmaceutically acceptable adjuvant.

Alternatively, this method comprises the step of administering to said mammal a composition comprising a compound of this invention; an additional anti-vascular hyperproliferative agent and a pharmaceutically acceptable adjuvant.

In another alternate preferred embodiment, these methods are useful for inhibiting tumors and cancer in a mammal. Such methods are useful in treating or preventing diseases, including, tumors and malignancies, such as lymphoma, leukemia and other forms of cancer.

These methods comprise the step of administering to the mammal a composition comprising a compound of this invention, and a pharmaceutically acceptable adjuvant. In a preferred embodiment, this particular method comprises the additional step of administering to said mammal a composition comprising an additional anti-tumor or anti-cancer agent and a pharmaceutically acceptable adjuvant.

Alternatively, this method comprises the step of administering to said mammal a composition comprising a compound of this invention; an additional-anti-tumor or anti-cancer agent and a pharmaceutically acceptable adjuvant.

In another alternate preferred embodiment, these methods are useful for inhibiting inflammation and inflammatory diseases in a mammal. Such methods are useful in treating or preventing diseases, including, osteoarthritis, acute pancreatitis, chronic pancreatitis, asthma and adult respiratory distress syndrome.

These methods comprise the step of administering to the mammal a composition comprising a compound of this invention, and a pharmaceutically acceptable adjuvant. In a preferred embodiment, this particular method comprises the additional step of administering to said mammal a composition comprising an anti-inflammatory agent and a pharmaceutically acceptable adjuvant.

In order that this invention be more fully understood, the following examples are set forth. These examples are for the purpose of illustration only and are not to be construed as limiting the scope of the invention in any way.

EXAMPLE 1

Synthesis of Compound 100

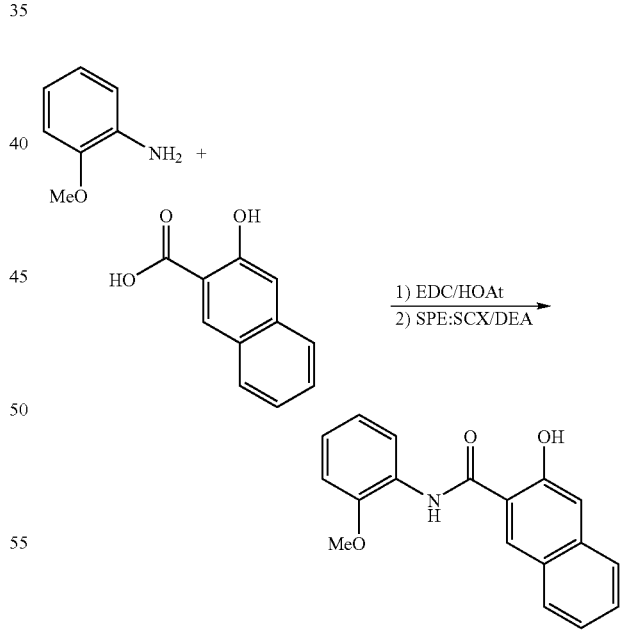

Solutions of acid (80 μL, 32 μmol) and aniline (100 μL, μmol) in THF were dispensed into a teflon 96-well plate. A solution containing 0.4M EDC.HCl and 0.4M HOAt in MeCN (100 μL, 40 μmol) was added and the reactions mixed in a vortex shaker for 5 h. MeOH (500 μL) was added.

HPLC-MS data: retention time in 0.1% TFA: 8.81 min

LRMS (EI): 294.1 (M+H, relative intensity 100%).

EXAMPLE 2

Synthesis of Compound 103:

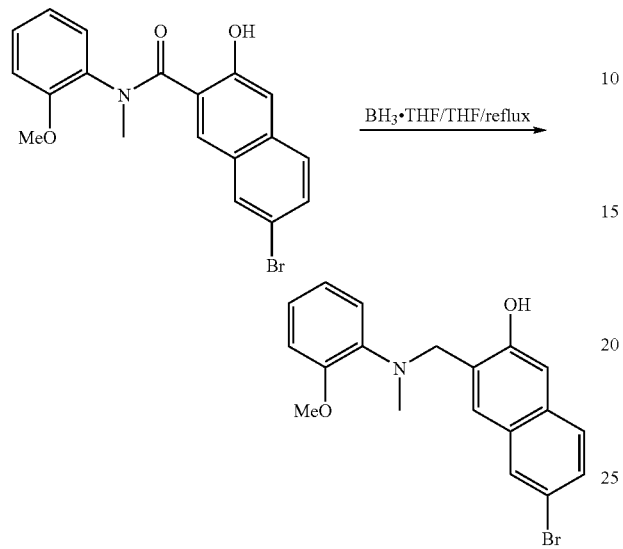

To a room temperature solution of the amide (65 mg, 0.168 mmole) in 5 ml of THF was added BH$_3$.THF (0.45 ml, 0.539 mmole). The resulting mixture was heated to reflux overnight, then cooled to room temperature, and concentrated in vacuo. The resulting crude product was diluted in 5 ml of saturated HCl in MeOH and heated to reflux for 3 hours. The resulting mixture was cooled to room temperature, diluted with ethyl acetate, washed successively with saturated NaHCO$_3$, water, brine, then dried over Na$_2$SO$_4$. The crude product was purified by silica-gel chromatography (9/1 hexanes/ether) to give 33 mg (53% yield) of the desired benzylamine.

$^1$H NMR (CDCL$_3$, 50.0 MHz): 10.51 (1H, broad s); 7.96 (1H; s); 7.67 (1H, d); 7.57 (1H, s); 7.55 (1H, dd); 7.34 (1H, s); 7.32 (1H, d); 7.26 (1H, dd); 7.09 (1H, dd); 7.04 (1H, d); 4.41 (2H, s); 4.06 (3H, s); 2.75 (3H, s).

EXAMPLE 3

Synthesis of Compound 302

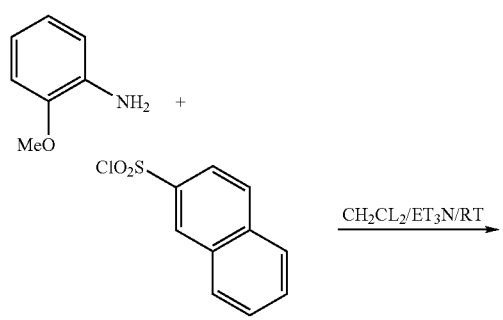

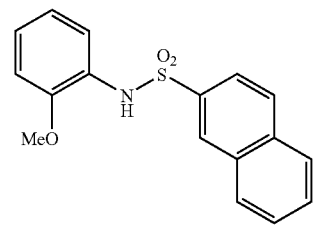

To a 0° C. solution of the sulfonyl chloride (100 mg, 0.44 mmoles) in CH$_2$Cl$_2$ (5 mL) was added o-anisidine (45 mL, 0.44 mmoles). The resulting mixture was allowed to warm to room temperature and stirred overnight. The crude reaction was diluted with ethyl acetate, washed with sat. NaHCO$_3$, 0.5 N HCl, brine, dried over Na$_2$SO$_4$, filtered, and concentrated in vacuo. The crude product was purified by MPLC to give the 88 mg (64%) of the desired sulfonamide.

$^1$H NMR (CDCl$_3$, 500 MHz): 8.31 (1H, s); 7.82 (3H, m); 7.70 (1H, d); 7.54 (3H, m); 7.06 (1H, s); 6.97 (1H, dd); 6.88 (1H, dd); 6.67 (1H, d); 3.56 (3H, s)

EXAMPLE 4

Synthesis of Compound 325

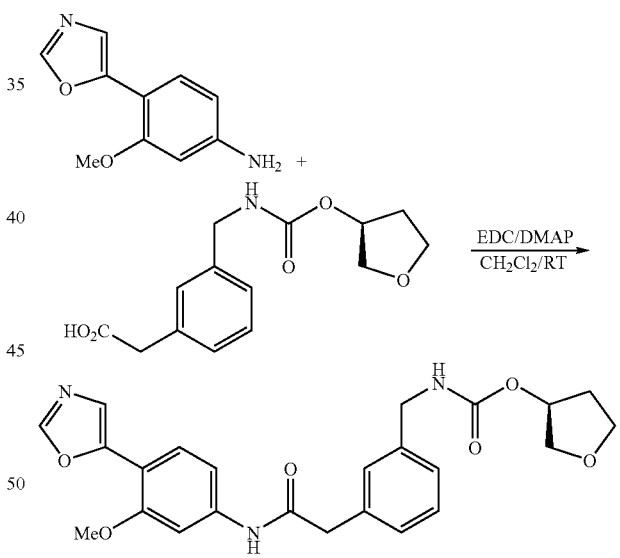

To a room temperature solution of the acid (76 mg, 0.272 mmole) in CH$_2$Cl$_2$ (4 ml) was added the aniline (57 mg, 0.30 mmole), EDC (104 mg, 0.544 mmole) and DMAP (catalytic amount). The resulting mixture was stirred at room temperature for 16 hours, then diluted with ethyl acetate and water. The phases were separated and the organic phase was washed with 1.0 N HCl, sat. NaHCO$_3$, brine, dried over Na$_2$SO$_4$, filtered and concentrated in vacuo. Crude product was purified via flash chromatography to give 56 mg (46%) of the desired amide as a white solid.

$^1$H NMR (DMSO-d$_6$, 500 MHz) 10.50 (1H, s); 8.40 (1H, s); 7.85 (1H, broad t); 7.65 (1H, d); 7.45 (1H, s); 7.50-7.35

(3H, m); 7.30-7.10 (4H, m); 5.15 (1H, broad m); 4.20 (2H, d); 3.90 (3H, s); 3.80-3.60 (4H, m); 2.10 (1H, m); 1.85 (1H, m).

EXAMPLE 5

Synthesis of Compound 326

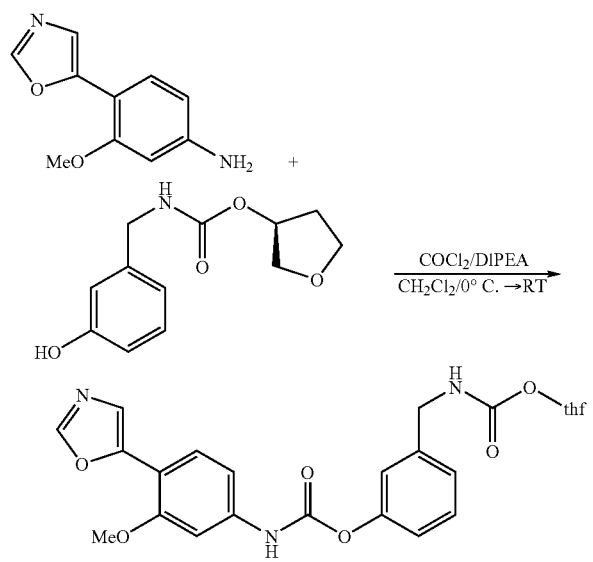

To a stirred, 0° C. solution of the phenol (86 mg, 0.362 mmole) in $CH_2Cl_2$ (1.5 mL) was added DIPEA (59 mL, 0.434 mmole) and phosgene (742 mL, 0.74 mmole, 1.0 M in PhMe). The resulting solution was warmed to room temperature, stirred for 2.5 hours, then concentrated in vacuo. The resulting chloroformate was diluted in $CH_2Cl_2$ (2 mL), cooled to 0° C., then treated with a $CH_2Cl_2$ solution of the aniline (83 mg, 0.434 mmole) and DIPEA (74 mL, 0.543 mmole). The resulting mixture was stirred at room temperature overnight, then diluted in ethyl acetate and water. The phases were separated, the organic phase washed with sat. $NaHCO_3$, brine, dried over $Na_2SO_4$, filtered, and concentrated in vacuo. The crude product was purified by flash chromatography to give 40 mg (24%) of the desired carbamate as a slightly yellow foam.

$^1$H NMR (DMSO-$d_6$, 500 MHz): 10.40 (1H, s), 8.38 (1H, s); 7.80 (1H, broad t); 7.62 (1H, d); 7.58 (1H, d); 7.45 (1H, s); 7.30-7.10 (5H, m); 5.12 (1H, m); 4.18 (2H, d); 3.90 (3H, s); 3.80-3.60 (4H, m); 3.65 (2H, s); 2.10 (1H, m); 1.95 (1H, m).

EXAMPLE 6

IMPDH Activity Inhibition Assay

IMP dehydrogenase activity was assayed following an adaptation of the method first reported by Magasanik. [B. Magasanik et al., *J. Biol. Chem.*, 226, p. 339 (1957), the disclosure of which is herein incorporated by reference]. Enzyme activity was measured spectrophotometrically, by monitoring the increase in absorbance at 340 nm due to the formation of NADH ($\epsilon$340 is 6220 $M^{-1}$ $cm^{-1}$). The reaction mixture contained 0.1 M Tris pH 8.0, 0.1 M KCl, 3 mM EDTA, 2 mM DTT, 0.1 M IMP and enzyme (IMPDH human type II) at a concentration of 15 to 50 nM. This solution is incubated at 37° C. for 10 minutes. The reaction is started by adding NAD to a final concentration of 0.1M and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 µl.

For the analysis of inhibitors, the compound in question is dissolved in DMSO to a final concentration of 20 mM and added to the initial assay mixture for preincubation with the enzyme at a final volume of 2-5% (v/v). The reaction is started by the addition of NAD, and the initial rates measured as above $K_i$ determinations are made by measuring the initial velocities in the presence of varying amounts of inhibitor and fitting the data using the tight-binding equations of Henderson (Henderson, P. J. F. (1972) Biochem. J. 127, 321].

These results are shown in Table 2. Category "A" indicates a $K_I$ of less than 10 µM, category "B" indicates a $K_I$ of between 10 and 20 µM, category "C" indicates a $K_I$ greater than 20 µM.

TABLE 2

| IMPDH inhibitory activity. | |
|---|---|
| Compound | Ki |
| 100 | A |
| 101 | B |
| 102 | A |
| 103 | B |
| 104 | B |
| 105 | B |
| 106 | B |
| 107 | B |
| 108 | B |
| 109 | A |
| 110 | B |
| 111 | A |
| 112 | B |
| 113 | A |
| 114 | A |
| 115 | A |
| 116 | C |
| 117 | C |
| 118 | B |
| 119 | C |
| 120 | B |
| 121 | B |
| 122 | B |
| 123 | A |
| 124 | A |
| 125 | B |
| 126 | A |
| 127 | A |
| 128 | B |
| 129 | B |
| 130 | B |
| 131 | B |
| 132 | B |
| 133 | B |
| 134 | B |
| 135 | B |
| 136 | B |
| 137 | B |
| 138 | A |
| 139 | A |
| 140 | A |
| 141 | A |
| 142 | B |
| 143 | A |
| 144 | B |
| 145 | B |
| 146 | B |
| 147 | A |
| 148 | B |
| 149 | B |
| 150 | B |

TABLE 2-continued

IMPDH inhibitory activity.

| Compound | Ki |
|---|---|
| 151 | A |
| 152 | B |
| 153 | A |
| 154 | B |
| 155 | B |
| 156 | B |
| 157 | B |
| 159 | B |
| 160 | B |
| 161 | A |
| 162 | B |
| 163 | B |
| 164 | A |
| 165 | B |
| 166 | B |
| 167 | B |
| 168 | B |
| 169 | A |
| 170 | A |
| 171 | B |
| 172 | A |
| 173 | B |
| 174 | B |
| 175 | A |
| 177 | B |
| 178 | A |
| 179 | B |
| 180 | B |
| 181 | A |
| 182 | A |
| 183 | A |
| 184 | B |
| 185 | A |
| 186 | B |
| 187 | B |
| 188 | B |
| 190 | C |
| 191 | C |
| 192 | C |
| 193 | B |
| 194 | C |
| 195 | B |
| 196 | B |
| 197 | C |
| 198 | C |
| 199 | C |
| 200 | B |
| 201 | B |
| 202 | C |
| 203 | C |
| 204 | C |
| 300 | B |
| 301 | B |
| 302 | B |
| 303 | C |
| 304 | C |
| 305 | A |
| 306 | B |
| 307 | B |
| 308 | B |
| 309 | B |
| 310 | B |
| 311 | B |
| 312 | B |
| 313 | B |
| 314 | B |
| 315 | B |
| 316 | B |
| 317 | B |
| 318 | B |
| 319 | B |
| 320 | B |
| 321 | B |
| 322 | B |
| 323 | B |
| 324 | B |

TABLE 2-continued

IMPDH inhibitory activity.

| Compound | Ki |
|---|---|
| 325 | A |
| 326 | A |

Other compounds of this invention will also have IMPDH inhibitory activity.

EXAMPLE 7

Anti-Viral Assays

The anti-viral efficacy of compounds may be evaluated in various in vitro ad in vivo assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

The invention claimed is:

1. A composition comprising:
   a) a compound selected from the group consisting of:

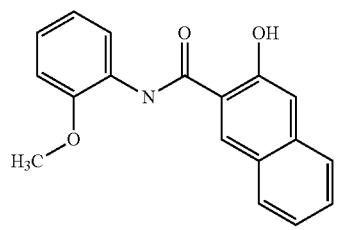

100

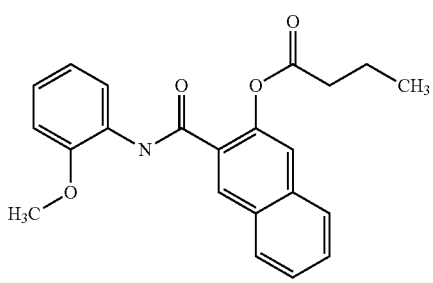

101

102
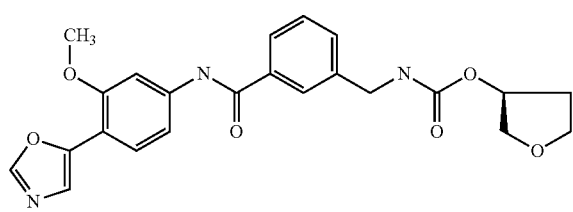
103
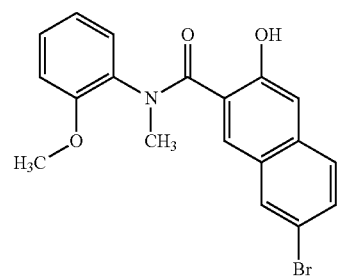
104
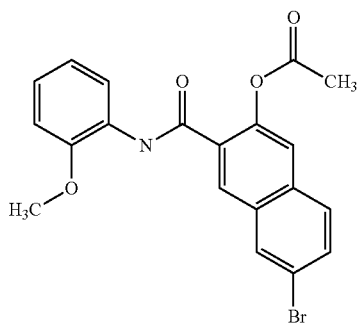
105
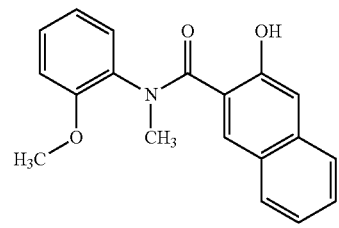
106
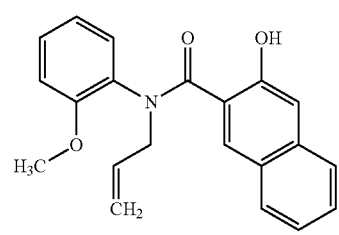
107
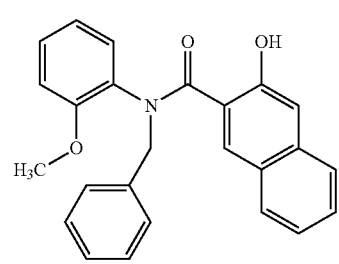
109
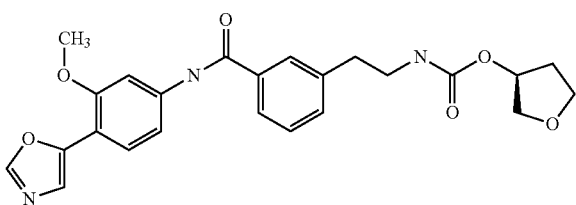
110
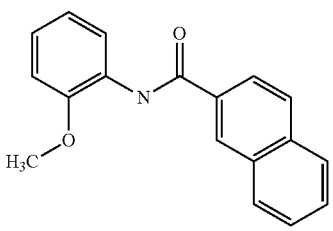
111
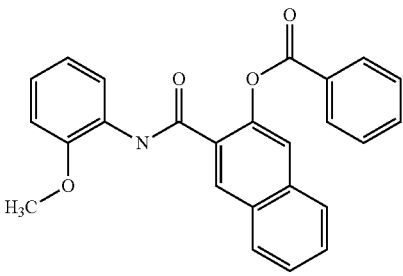
112
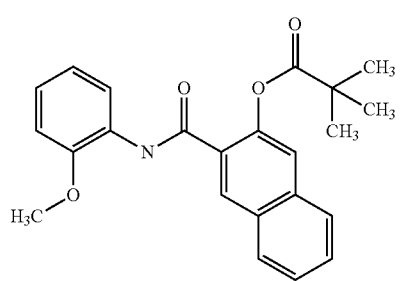
113
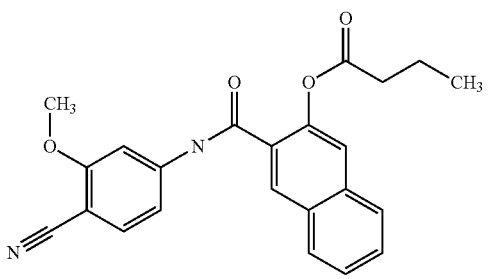
114
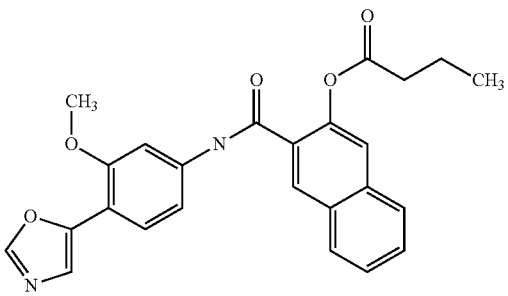

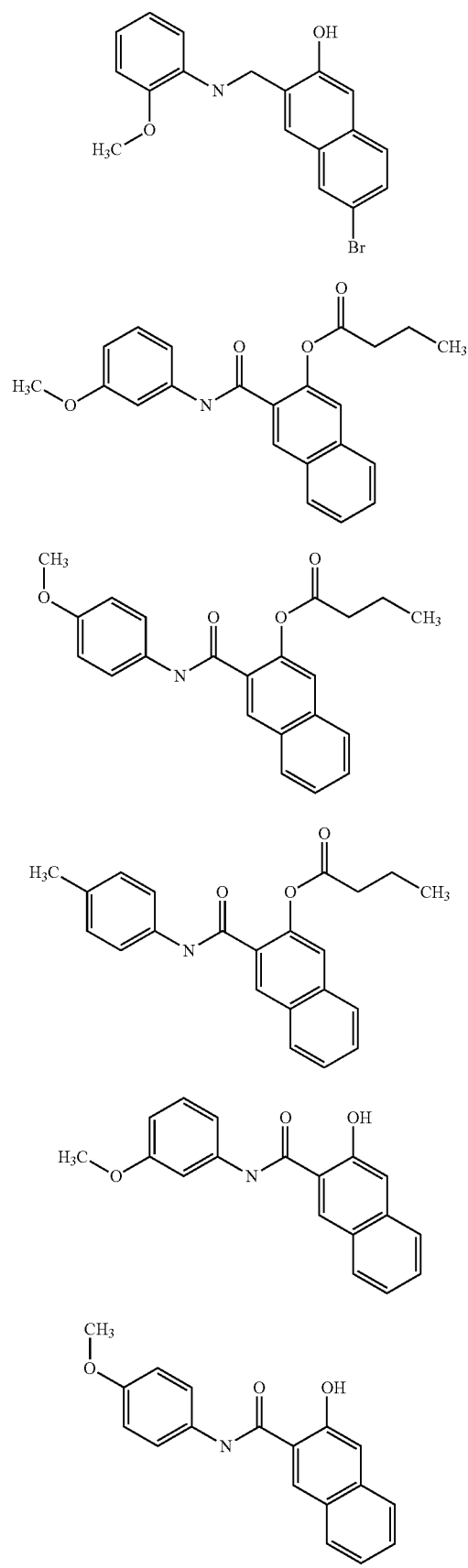
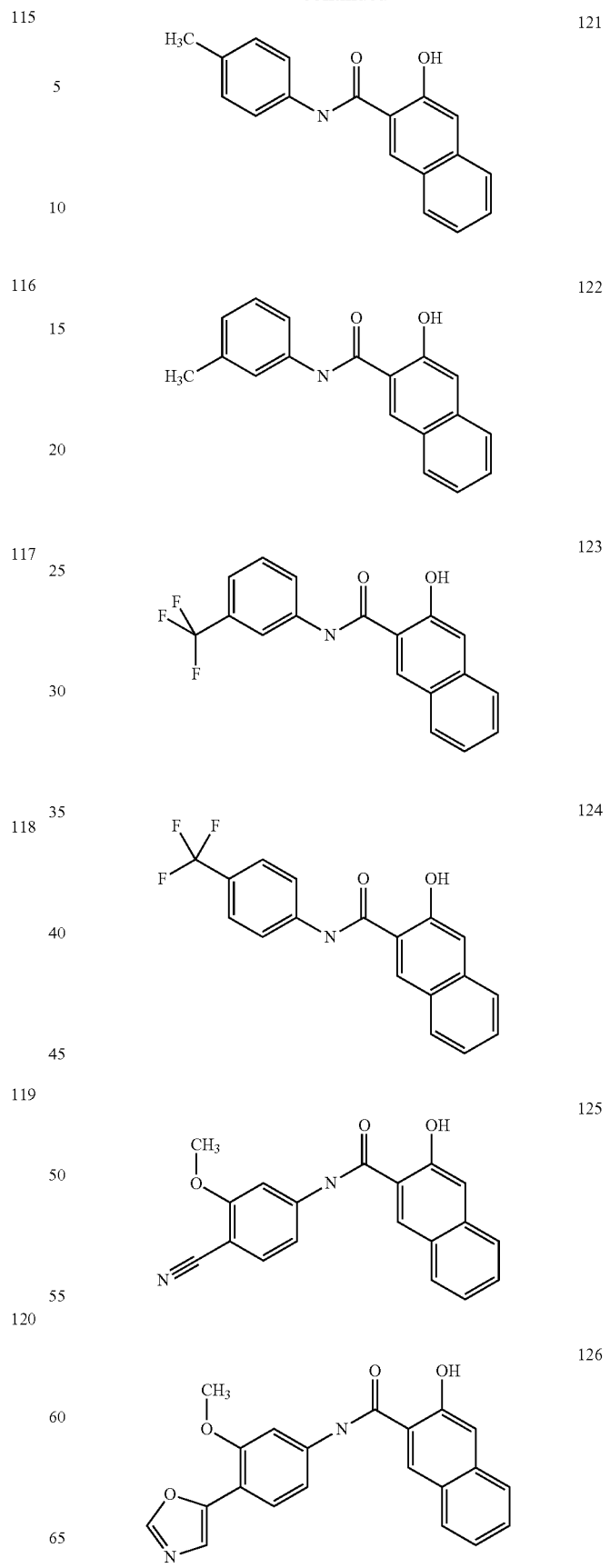

127 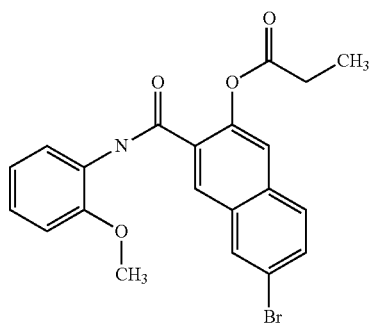
128 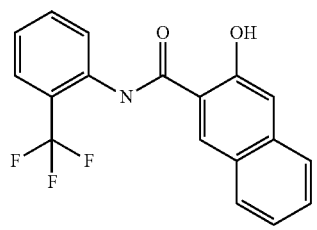
129 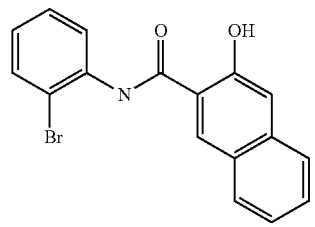
130 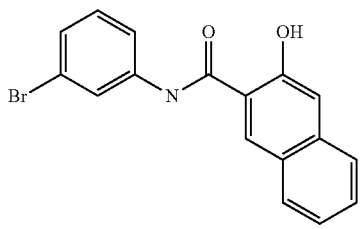
131 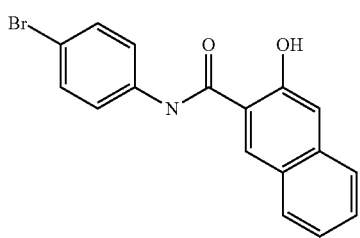
132 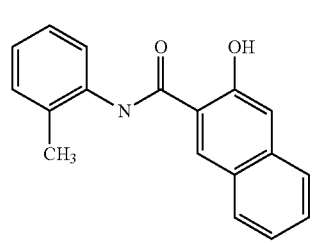
134 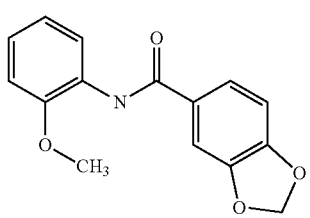
135 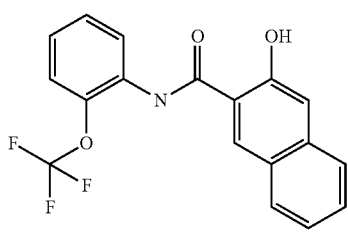
136 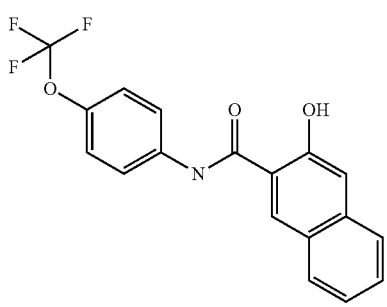
137 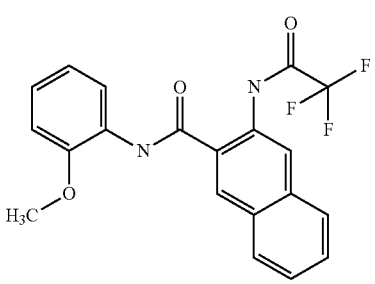
138 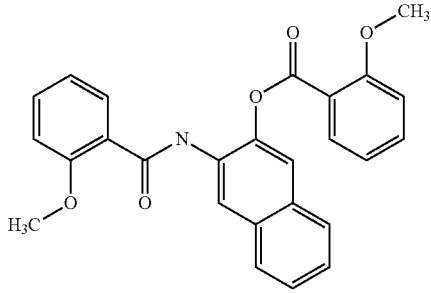
139 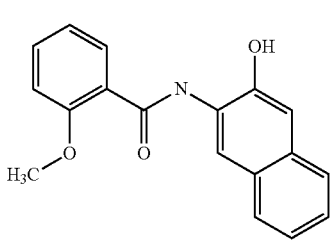

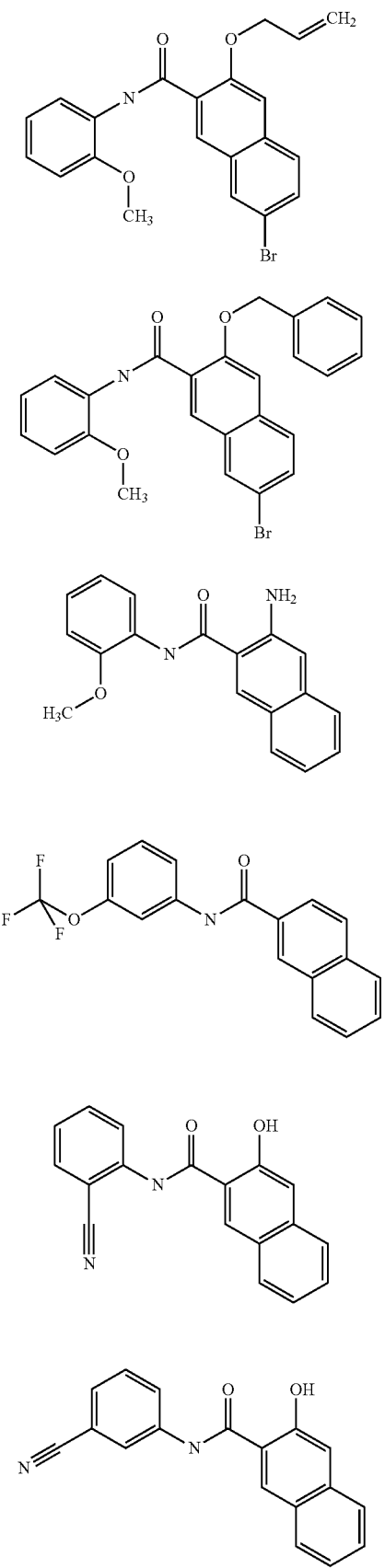
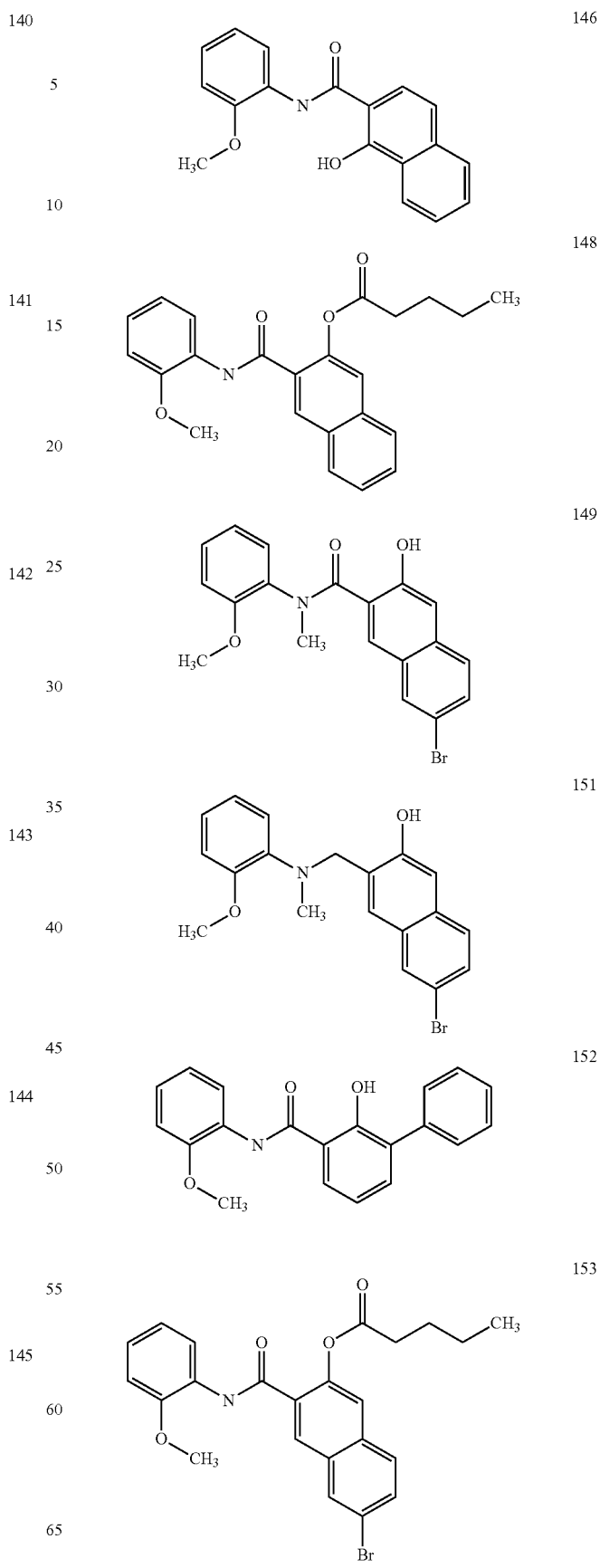

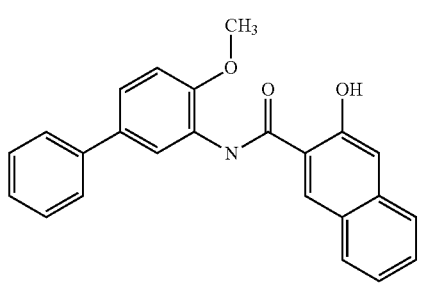
154
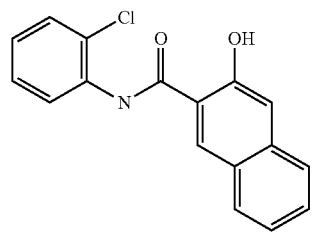
155
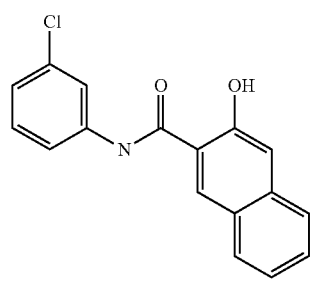
156
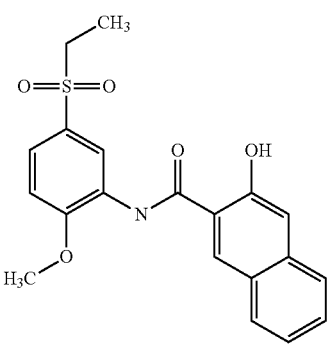
159
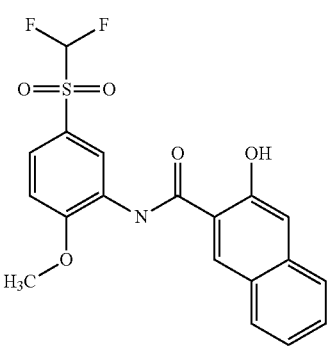
160
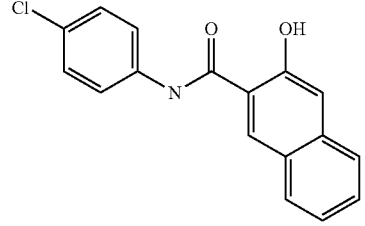
161
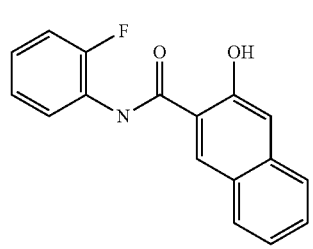
162
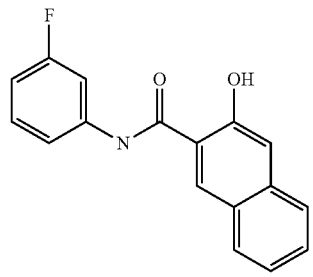
163
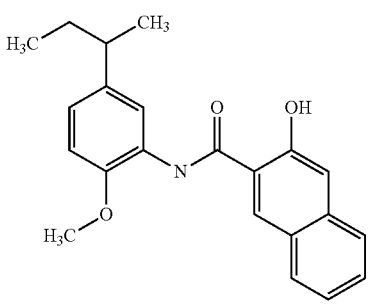
164
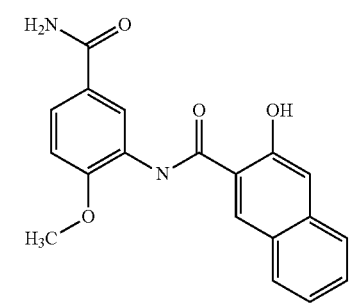
165
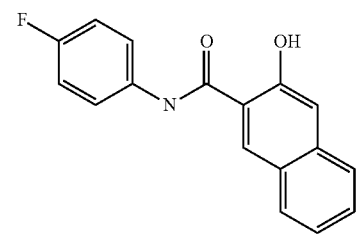
166

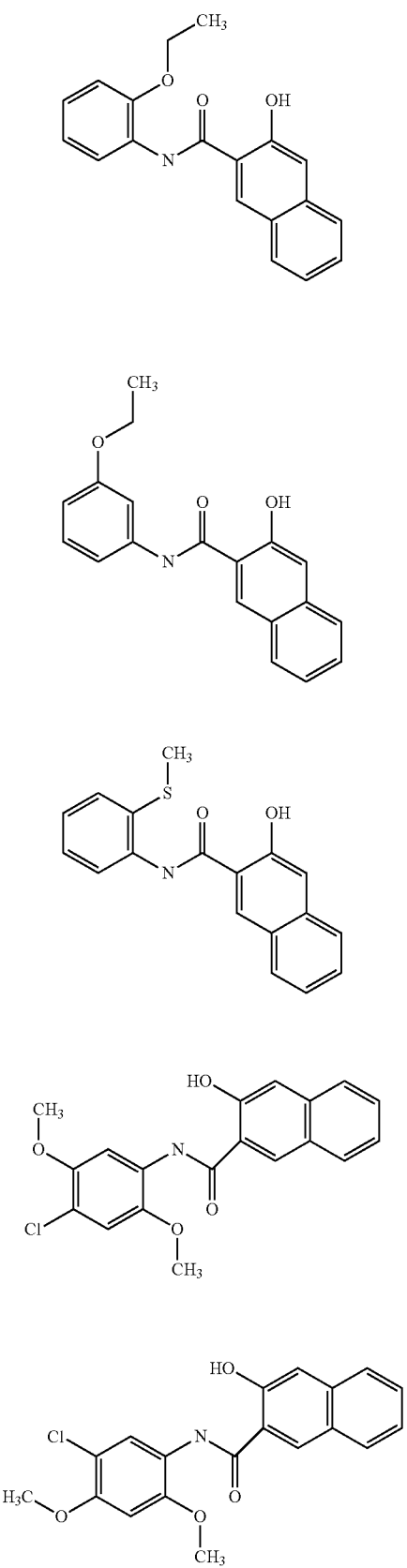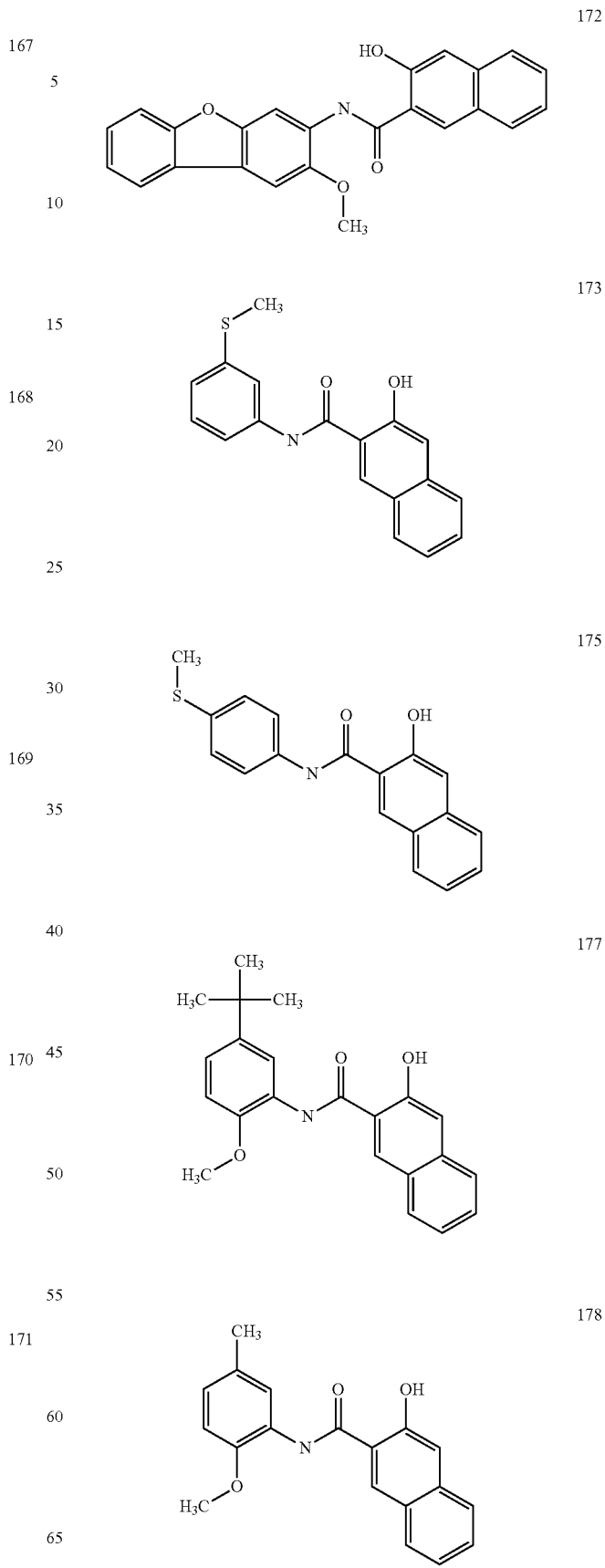

179
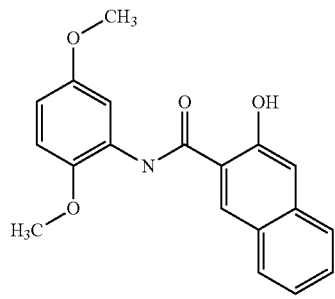
180
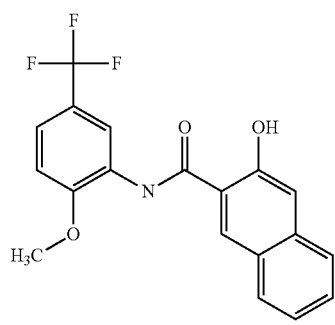
181
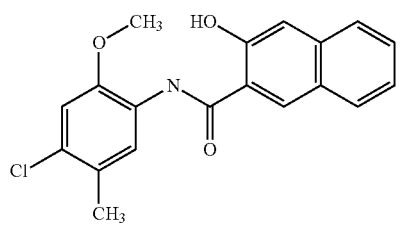
182
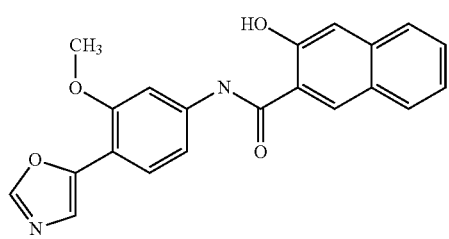
183
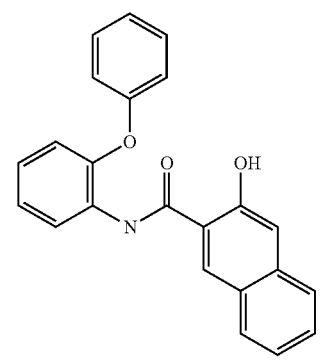
184
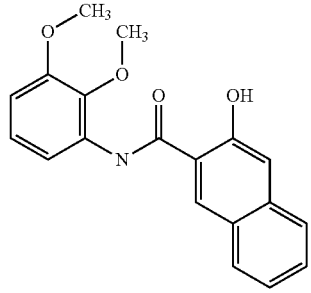
185
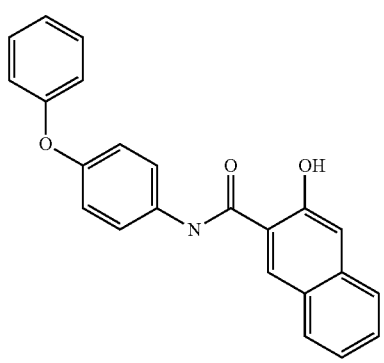
186
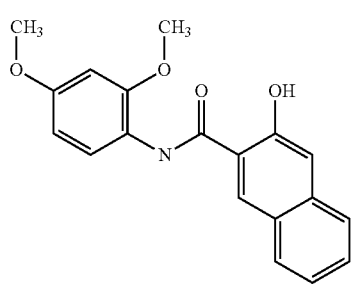
187
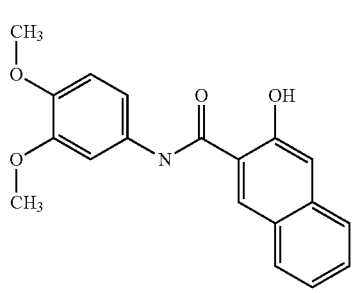
188
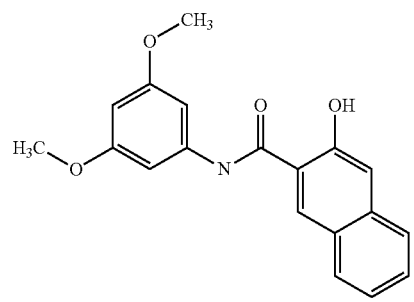

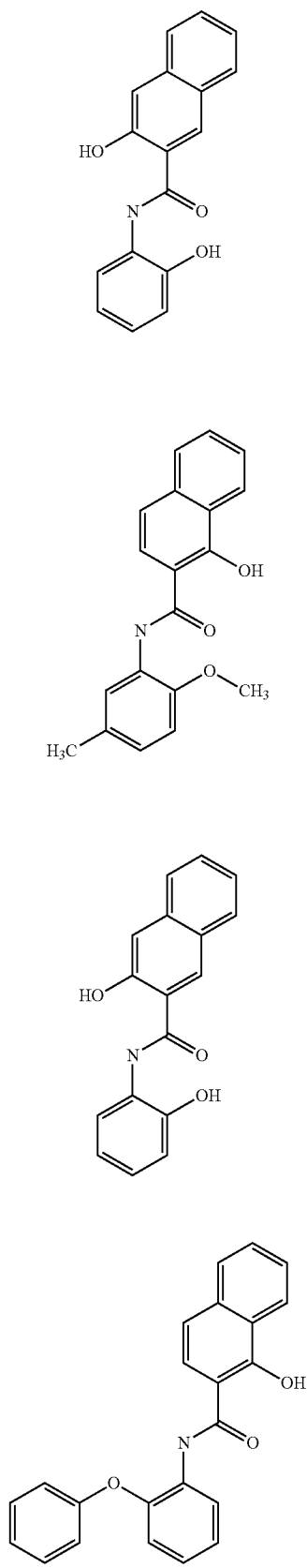
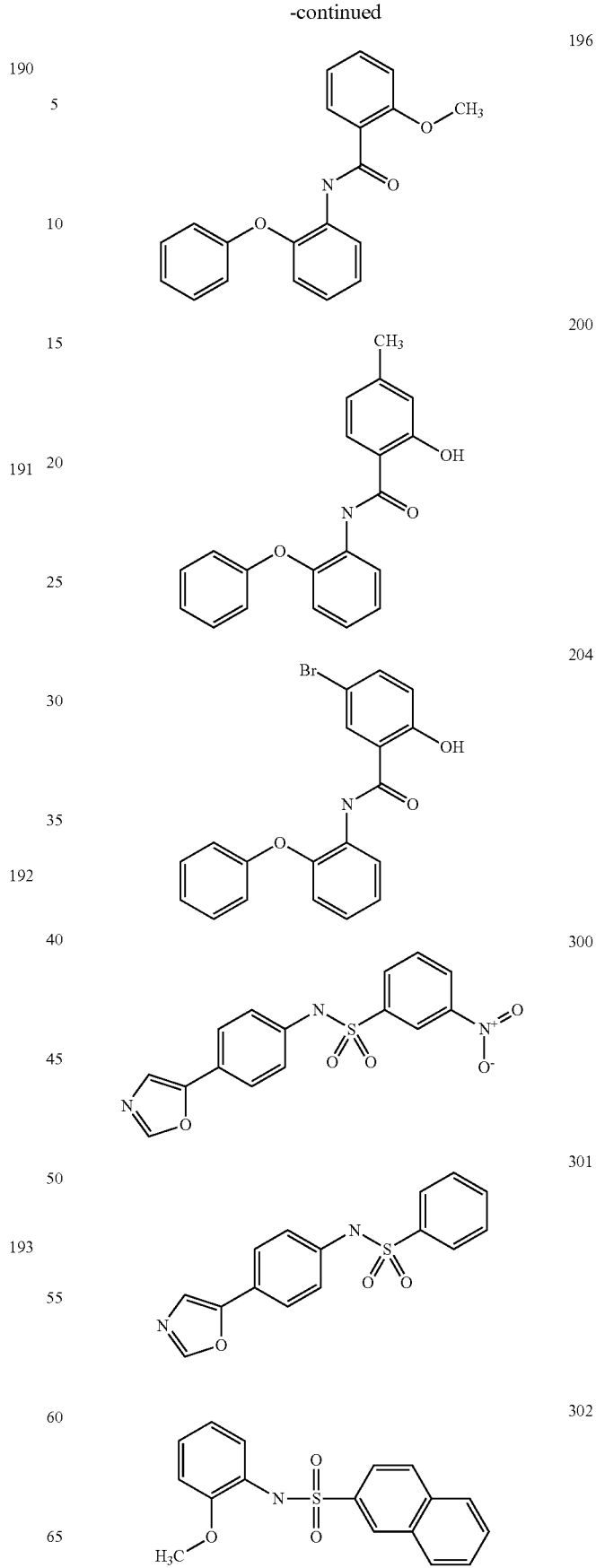

-continued
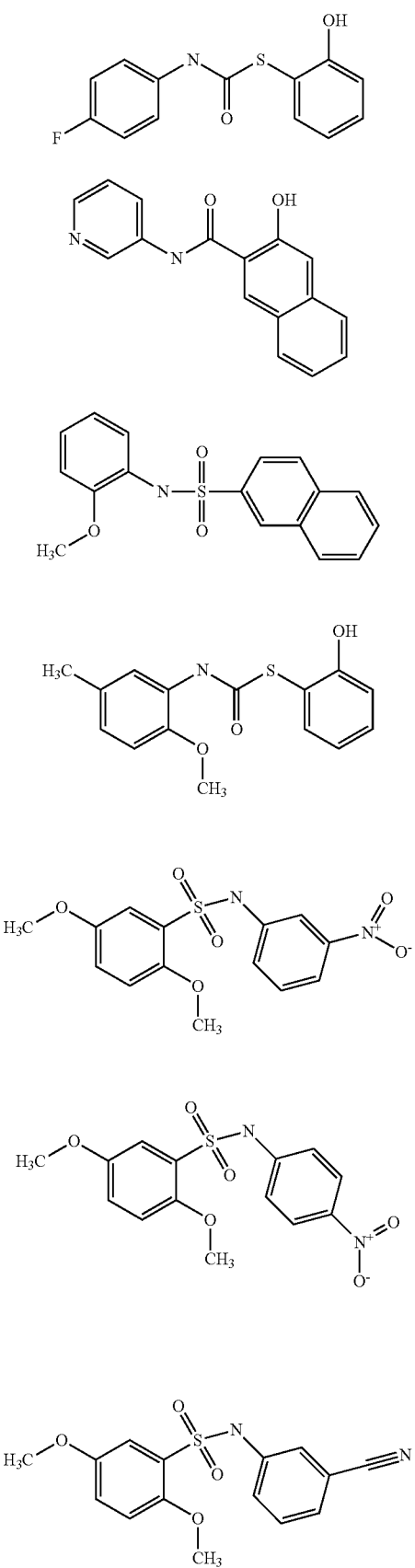
303
304
305
306
307
308
309
-continued
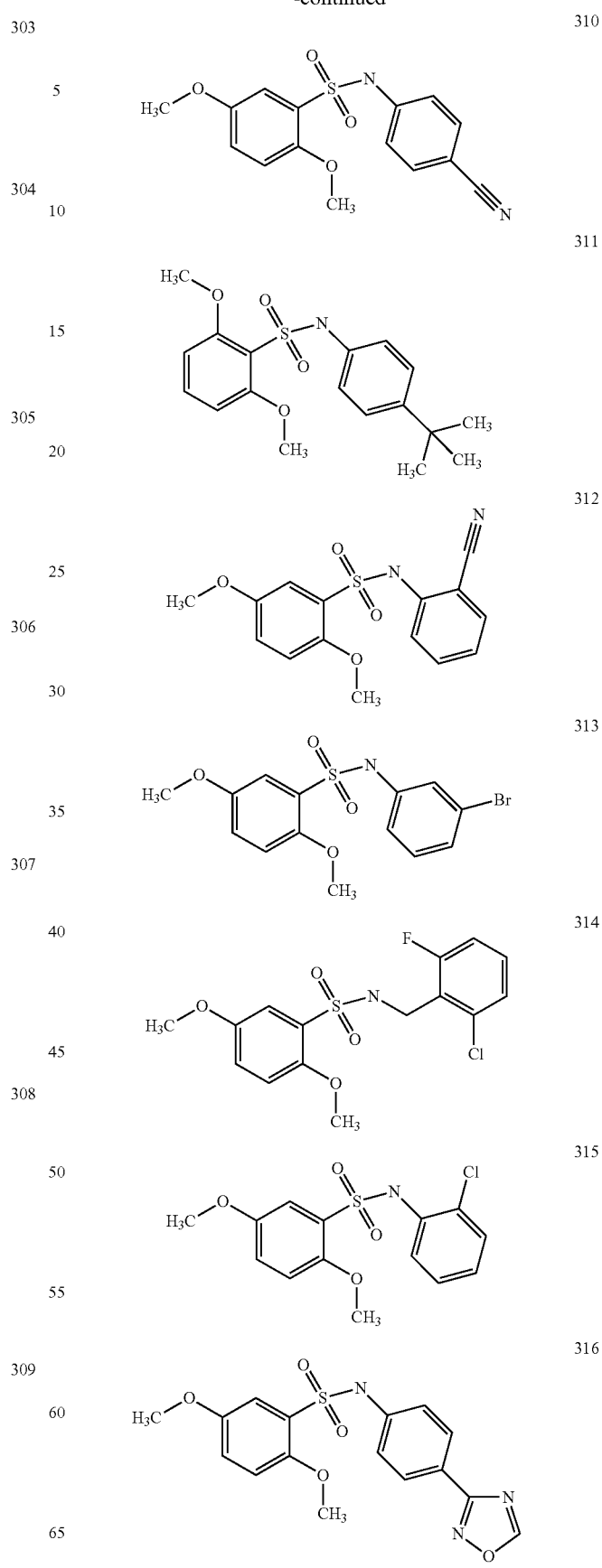
310
311
312
313
314
315
316

-continued
317 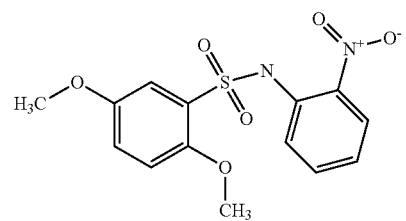
318 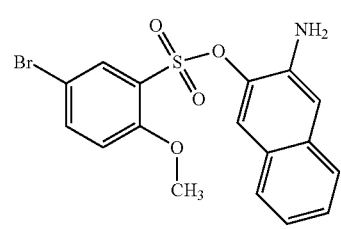
319 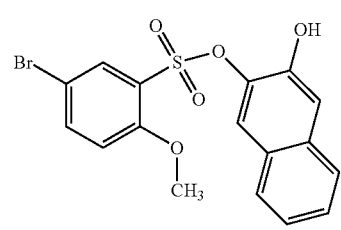
320 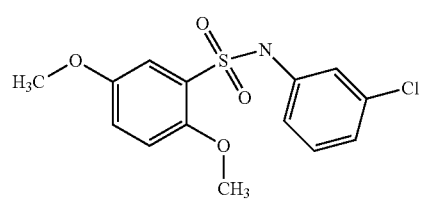
321 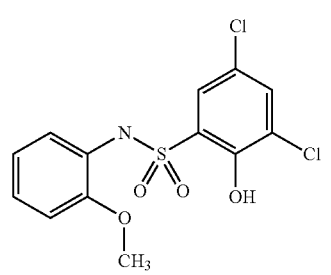
-continued
322 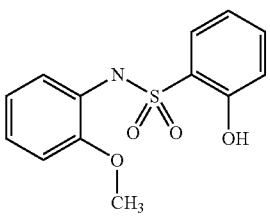
323 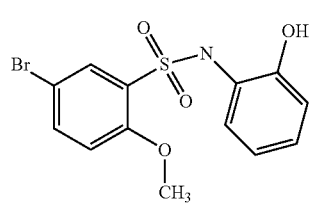
324 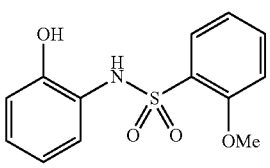
325 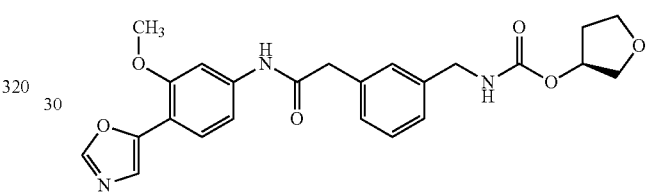
326 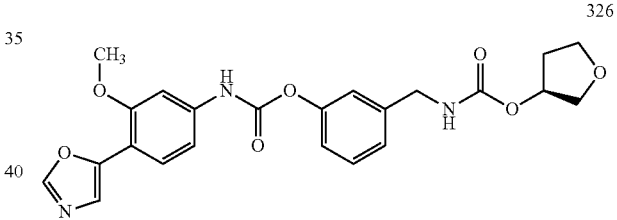
and
b) a carrier, adjuvant, or vehicle, which is pharmaceutically acceptable for oral administration or administration by injection.
* * * * *